United States Patent
Mack et al.

(10) Patent No.: US 6,455,668 B1
(45) Date of Patent: Sep. 24, 2002

(54) METHODS OF DIAGNOSING COLORECTAL CANCER, COMPOSITIONS, AND METHODS OF SCREENING FOR COLORECTAL CANCER MODULATORS

(75) Inventors: David Mack, Menlo Park; Kurt C. Gish, San Francisco; Keith E. Wilson, Redwood City, all of CA (US)

(73) Assignee: Eos Biotechnology, Inc., South San Francisco, CA (US)

( * ) Notice: Subject to any disclaimer, the term of this patent is extended or adjusted under 35 U.S.C. 154(b) by 0 days.

(21) Appl. No.: 09/656,002

(22) Filed: Sep. 6, 2000

Related U.S. Application Data

(63) Continuation of application No. 09/525,993, filed on Mar. 15, 2000, which is a continuation-in-part of application No. 09/493,444, filed on Jan. 28, 2000.

(51) Int. Cl.$^7$ .......................... A61K 38/00; C12Q 1/68; C12P 19/34; C07H 21/02; C07K 1/00
(52) U.S. Cl. .......................... 530/300; 435/6; 435/91.1; 536/23.1; 530/351
(58) Field of Search .......................... 435/6, 91.1, 91.2; 536/23.1; 530/350, 351

(56) References Cited

U.S. PATENT DOCUMENTS 6,203,979 B1 * 3/2001 Bandman et al. .............. 435/6

FOREIGN PATENT DOCUMENTS

| WO | 92/15602 | 9/1992 |
|---|---|---|
| WO | 97/41224 | 11/1997 |
| WO | 97/42209 | 11/1997 |
| WO | 99/04030 | 1/1999 |

OTHER PUBLICATIONS

"Molecular Biology of Colorectal Cancer," *Curr. Probl. Cancer*, 238–299 (Sep./Oct. 1997).

Liefers et al., "Micrometastases and Survival in Stage II Colorectal Cancer," *New England J. of Med.*, 339(4):223–228 (1998).

Payne et al., "Primiany Structure, Functional Expression, and Chromosomal Localization of the Bumetanide–sensitive Na–K–CL Cotransporter in Human Colon," The Journal of Biological Chemistry, 270(30): 17977–17985 (1995).

Pallela et al., "99mTc–Labeled Vasoactive Intestinal Peptide Receptor Agonist: Functional Studies," The Journal of Nuclear Medicine, 40(2):352–360 (1999).

Yamamoto et al., "Clinical application of chimeric monoclonal antibody A7–NCS conjugate," Biotherapy, 10(3): 365–367 (1996).

King et al., "Expression, purification and characterization of a mouse–human chimeric antibody and chimeric Fab' fragment," Biochemical Journal, 281, part 2, 317–323 (1992).

NCBI Protein Database Accession No. AAF31436 type II membrane serine protease [Homo sapiens]. Smeekens et al. (Dec. 14, 1999).

* cited by examiner

*Primary Examiner*—John S. Brusca
*Assistant Examiner*—Young Kim
(74) *Attorney, Agent, or Firm*—Townsend & Townsend & Crew LLP

(57) ABSTRACT

Described herein are methods that can be used for diagnosis and prognosis of colorectal cancer. Also described herein are methods that can be used to screen candidate bioactive agents for the ability to modulate colorectal cancer. Additionally, methods and molecular targets (genes and their products) for therapeutic intervention in colorectal cancer are described.

16 Claims, 3 Drawing Sheets

GAGAGGCAGCAGCTTGTTCAGCGGACAAGGATGCTGGGCGTGAGGGACCAAGGCCTGCCCTGCACTCGGG
CCTCCTCCAGCCAGTGCTGACCAGGGACTTCTGACCTGCTGGCCAGCCAGGACCTGTGTGGGGAGGCCCT
CCTGCTGCCTTGGGGTGACAATCTCAGCTCCAGGCTACAGGGAGACCGGGAGGATCACAGAGCCAGCATG
GTACAGGATCCTGACAGTGATCAACCTCTGAACAGCCTCGATGTCAAACCCCTGCGCAAACCCCGTATCC
CCATGGAGACCTTCAGAAAGTGTGGGGATCCCCATCATCATAGCACTACTGAGCCTGGCGAGTATCATCA
TTGTGGTTGTCCTCATCAAGGTGATTCTGGATAAATACTACTTCCTCTGCGGGCAGCCTCTCCACTTCAT
CCCGAGGAAGCAGCTGTGTGACGGAGAGCTGGACTGTCCCTTGGGGGAGGACGAGGAGCACTGTGTCAAG
AGCTTCCCCGAAGGGCCTGCAGTGGCAGTCCGCCTCTCCAAGGACCGATCCACACTGCAGGTGCTGGACT
CGGCCACAGGGAACTGGTTCTCTGCCTGTTTCGACAACTTCACAGAAGCTCTCGCTGAGACAGCCTGTAG
GCAGATGGGCTACAGCAGCAAACCCACTTTCAGAGCTGTGGAGATTGGCCCAGACCAGGATCTGGATGTT
GTTGAAATCACAGAAAACAGCCAGGAGCTTCGCATGCGGAACTCAAGTGGGCCCTGTCTCTCAGGCTCCC
TGGTCTCCCTGCACTGTCTTGCCTGTGGGAAGAGCCTGAAGACCCCCGTGTGGTGGGTGGGGAGGAGGC
CTCTGTGGATTCTTGGCCTTGGCAGGTCAGCATCCAGTACGACAAACAGCACGTCTGTGGAGGGAGCATC
CTGGACCCCCACTGGGTCCTCACGGCAGCCCACTGCTTCAGGAAACATACCGATGTGTTCAACTGGAAGG
TGCGGGCAGGCTCAGACAAACTGGGCAGCTTCCCATCCCTGGCTGTGGCCAAGATCATCATCATTGAATT
CAACCCCATGTACCCCAAAGACAATGACATCGCCCTCATGAAGCTGCAGTTCCCACTCACTTTCTCAGGC
ACAGTCAGGCCCATCTGTCTGCCCTTCTTTGATGAGGAGCTCACTCCAGCCACCCCACTCTGGATCATTG
GATGGGGCTTTACGAAGCAGAATGGAGGGAAGATGTCTGACATACTGCTGCAGGCGTCAGTCCAGGTCAT
TGACAGCACACGGTGCAATGCAGACGATGCGTACCAGGGGGAAGTCACCGAGAAGATGATGTGTGCAGGC
ATCCCGGAAGGGGGTGTGGACACCTGCCAGGGTGACAGTGGTGGGCCCCTGATGTACCAATCTGACCAGT
GGCATGTGGTGGGCATCGTTAGCTGGGCTATGGCTGCGGGGGCCCGAGCACCCCAGGAGTATACACCAA
GGTCTCAGCCTATCTCAACTGGATCTACAATGTCTGGAAGGCTGAGCTGTAATGCTGCTGCCCCTTTGCA
GTGCTGGGAGCCGCTTCCTTCCTGCCCTGCCCACCTGGGGATCCCCCAAAGTCAGACACAGAGCAAGAGT
CCCCTTGGGTACACCCCTCTGCCCACAGCCTCAGCATTTCTTGGAGCAGCAAAGGGCCTCAATTCCTGTA
AGAGACCCTCGCAGCCCAGAGGCGCCCAGAGGAAGTCAGCAGCCCTAGCTCGGCCACACTTGGTGCTCCC
AGCATCCCAGGGAGAGACACAGCCCACTGAACAAGGTCTCAGGGGTATTGCTAAGCCAAGAAGGAACTTT
CCCACACTACTGAATGGAAGCAGGCTGTCTTGTAAAAGCCCAGATCACTGTGGGCTGGAGAGGAGAAGGA
AAGGGTCTGCGCCAGCCCTGTCCGTCTTCACCCATCCCCAAGCCTACTAGAGCAAGAAACCAGTTGTAAT
ATAAAATGCACTGCCCTACTGTTGGTATGACTACCGTTACCTACTGTTGTCATTGTTATTACAGCTATGG
CCACTATTATTAAAGAGCTGTGTAACATCAAAAAAAAAAAAAAAAAAA

FIGURE 1

MSNPCANPVSPWRPSESVGIPLIIALLSLASIIIVVVLIKVILDKYYFLCGQPLHFIPRKQLCDGELDCPL
GEDEEHCVKSFPEGPAVAVRLSKDRSTLQVLDSATGNWFSACFDNFTEALAETACRQMGYSSKPTFRAVEI
GPDQDLDVVEITENSQELRMRNSSGPCLSGSLVSLHCLACGKSLKTPRVVGGEEASVDSWPWQVSIQYDKQ
HVCGGSILDPHWVLTAAHCFRKHTDVFNWKVRAGSDKLGSFPSLAVAKIIIIEFNPMYPKDNDIALMKLQF
PLTFSGTVRPICLPFFDEELTPATPLWIIGWGFTKQNGGKMSDILLQASVQVIDSTRCNADDAYQGEVTEK
MMCAGIPEGGVDTCQGDSGGPLMYQSDQWHVVGIVSWGYGCGGPSTPGVYTKVSAYLNWIYNVWKAEL.

FIGURE 2

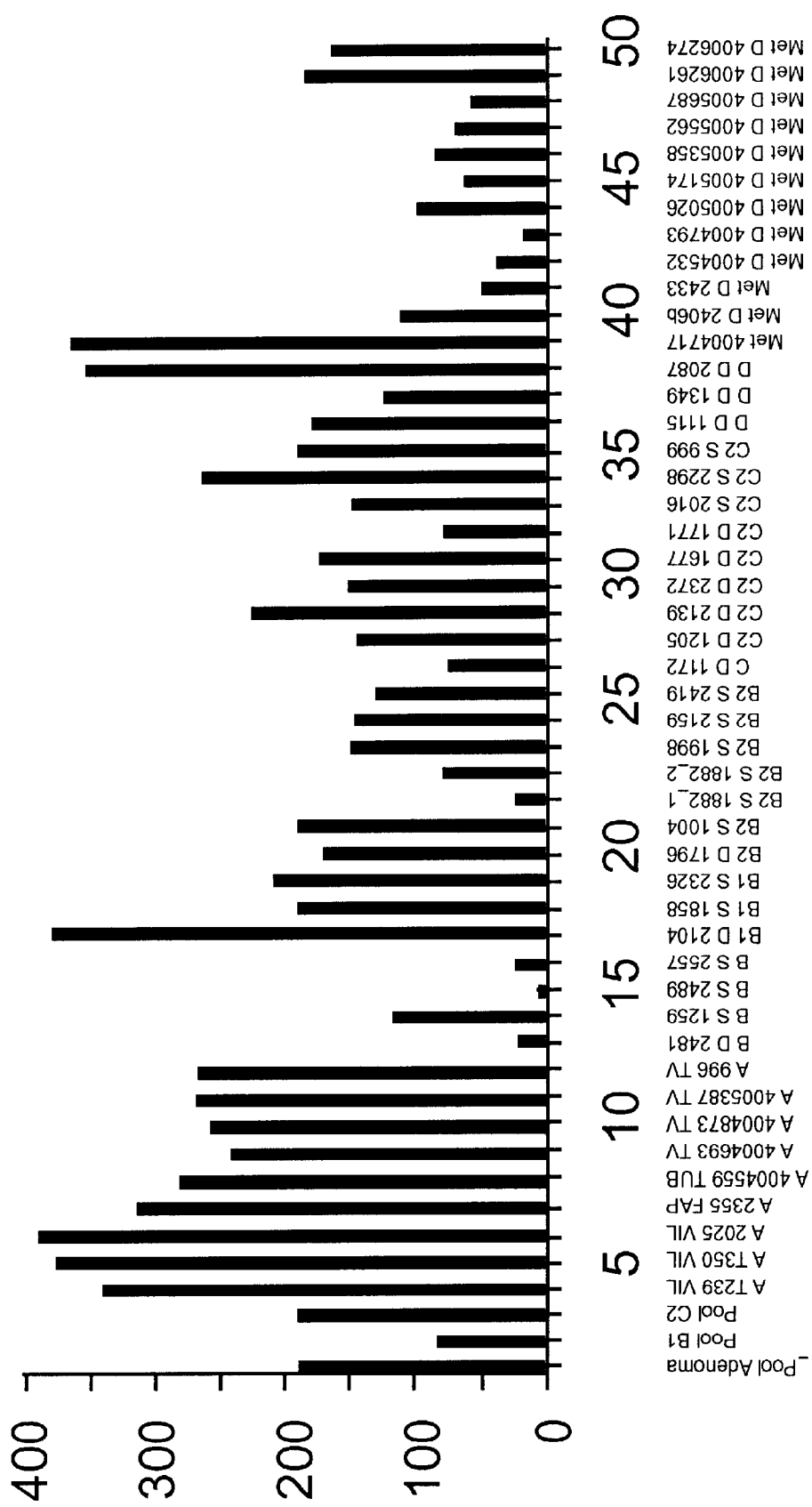
FIG. 3 (1 of 2)

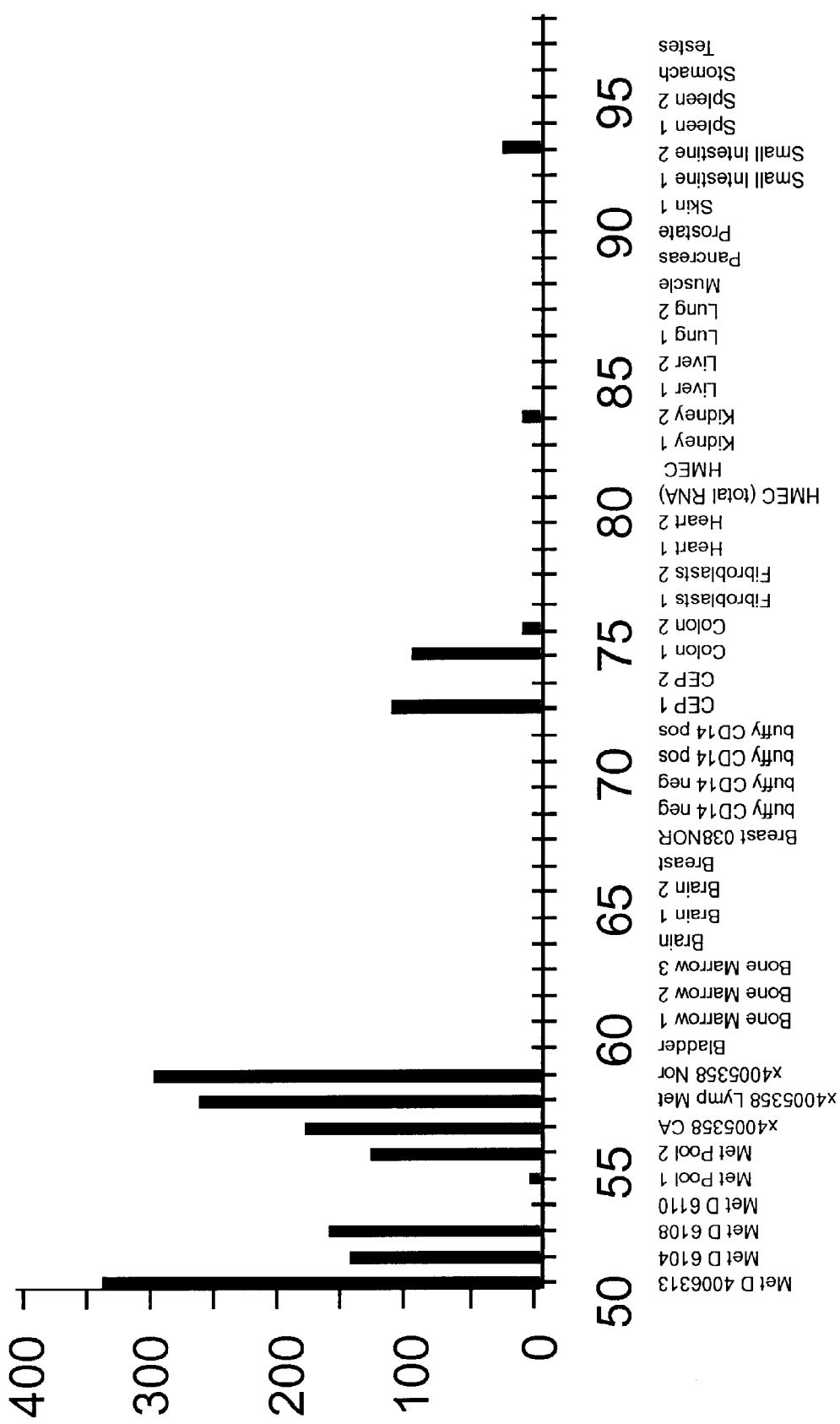
FIG. 3 (2 of 2)

SEQUENCE LISTING

<160> NUMBER OF SEQ ID NOS: 3

<210> SEQ ID NO 1
<211> LENGTH: 2079
<212> TYPE: DNA
<213> ORGANISM: Homo sapiens

<400> SEQUENCE: 1

```
gagaggcagc agcttgttca gcggacaagg atgctgggcg tgagggacca aggcctgccc      60
tgcactcggg cctcctccag ccagtgctga ccagggactt ctgacctgct ggccagccag     120
gacctgtgtg gggaggccct cctgctgcct tggggtgaca atctcagctc caggctacag     180
ggagaccggg aggatcacag agccagcatg gtacaggatc ctgacagtga tcaacctctg     240
aacagcctcg atgtcaaacc cctgcgcaaa ccccgtatcc ccatggagac cttcagaaag     300
tgtggggatc cccatcatca tagcactact gagcctggcg agtatcatca ttgtggttgt     360
cctcatcaag gtgattctgg ataaatacta cttcctctgc gggcagcctc tccacttcat     420
cccgaggaag cagctgtgtg acggagagct ggactgtccc ttgggggagg acgaggagca     480
ctgtgtcaag agcttccccg aagggcctgc agtggcagtc cgcctctcca aggaccgatc     540
cacactgcag gtgctggact cggccacagg gaactggttc tctgcctgtt tcgacaactt     600
cacagaagct ctcgctgaga cagcctgtag gcagatgggc tacagcagca acccactttt     660
cagagctgtg gagattggcc cagaccagga tctggatgtt gttgaaatca cagaaaacag     720
ccaggagctt cgcatgcgga actcaagtgg gccctgtctc tcaggctccc tggtctccct     780
gcactgtctt gcctgtggga agagcctgaa gacccccgt gtggtgggtg gggaggaggc     840
ctctgtggat tcttggcctt ggcaggtcag catccagtac gacaaacagc acgtctgtgg     900
agggagcatc ctggaccccc actgggtcct cacggcagcc cactgcttca ggaaacatac     960
cgatgtgttc aactggaagg tgcgggcagg ctcagacaaa ctgggcagct cccatccct   1020 ggctgtggcc aagatcatca tcattgaatt caaccccatg taccccaaag acaatgacat   1080
cgccctcatg aagctgcagt tcccactcac ttctcaggc acagtcaggc ccatctgtct   1140
gcccttcttt gatgaggagc tcactccagc caccccactc tggatcattg atggggctt   1200 tacgaagcag aatggaggga agatgtctga catactgctg caggcgtcag tccaggtcat   1260
tgacagcaca cggtgcaatg cagacgatgc gtaccagggg gaagtcaccg agaagatgat   1320
gtgtgcaggc atcccggaag ggggtgtgga cacctgccag ggtgacagtg gtgggcccct   1380
gatgtaccaa tctgaccagt ggcatgtggt gggcatcgtt agctggggct atggctgcgg   1440
gggcccgagc accccaggag tatacaccaa ggtctcagcc tatctcaact ggatctacaa   1500
```

```
tgtctggaag gctgagctgt aatgctgctg cccctttgca gtgctgggag ccgcttcctt      1560
cctgccctgc ccacctgggg atcccccaaa gtcagacaca gagcaagagt cccttgggt      1620 acacccctct gcccacagcc tcagcatttc ttggagcagc aaagggcctc aattcctgta      1680
agagaccctc gcagcccaga ggcgcccaga ggaagtcagc agccctagct cggccacact      1740
tggtgctccc agcatcccag ggagagacac agcccactga acaaggtctc aggggtattg      1800
ctaagccaag aaggaacttt cccacactac tgaatggaag caggctgtct tgtaaaagcc      1860
cagatcactg tgggctggag aggagaagga aagggtctgc gccagccctg tccgtcttca      1920
cccatcccca agcctactag agcaagaaac cagttgtaat ataaaatgca ctgccctact      1980
gttggtatga ctaccgttac ctactgttgt cattgttatt acagctatgg ccactattat      2040
taaagagctg tgtaacatca aaaaaaaaaa aaaaaaaa                             2079
```

<210> SEQ ID NO 2
<211> LENGTH: 423
<212> TYPE: PRT
<213> ORGANISM: Homo sapiens

<400> SEQUENCE: 2

```
Met Ser Asn Pro Cys Ala Asn Pro Val Ser Pro Trp Arg Pro Ser Glu
1               5                   10                  15

Ser Val Gly Ile Pro Leu Ile Ile Ala Leu Leu Ser Leu Ala Ser Ile
            20                  25                  30

Ile Ile Val Val Val Leu Ile Lys Val Ile Leu Asp Lys Tyr Tyr Phe
        35                  40                  45

Leu Cys Gly Gln Pro Leu His Phe Ile Pro Arg Lys Gln Leu Cys Asp
    50                  55                  60

Gly Glu Leu Asp Cys Pro Leu Gly Glu Asp Glu His Cys Val Lys
65                  70                  75                  80

Ser Phe Pro Glu Gly Pro Ala Val Ala Val Arg Leu Ser Lys Asp Arg
                85                  90                  95

Ser Thr Leu Gln Val Leu Asp Ser Ala Thr Gly Asn Trp Phe Ser Ala
            100                 105                 110

Cys Phe Asp Asn Phe Thr Glu Ala Leu Ala Glu Thr Ala Cys Arg Gln
        115                 120                 125

Met Gly Tyr Ser Ser Lys Pro Thr Phe Arg Ala Val Glu Ile Gly Pro
    130                 135                 140

Asp Gln Asp Leu Asp Val Val Glu Ile Thr Glu Asn Ser Gln Glu Leu
145                 150                 155                 160

Arg Met Arg Asn Ser Ser Gly Pro Cys Leu Ser Gly Ser Leu Val Ser
                165                 170                 175

Leu His Cys Leu Ala Cys Gly Lys Ser Leu Lys Thr Pro Arg Val Val
            180                 185                 190

Gly Gly Glu Glu Ala Ser Val Asp Ser Trp Pro Trp Gln Val Ser Ile
        195                 200                 205

Gln Tyr Asp Lys Gln His Val Cys Gly Gly Ser Ile Leu Asp Pro His
    210                 215                 220

Trp Val Leu Thr Ala Ala His Cys Phe Arg Lys His Thr Asp Val Phe
225                 230                 235                 240

Asn Trp Lys Val Arg Ala Gly Ser Asp Lys Leu Gly Ser Phe Pro Ser
                245                 250                 255

Leu Ala Val Ala Lys Ile Ile Ile Ile Glu Phe Asn Pro Met Tyr Pro
            260                 265                 270
```

```
Lys Asp Asn Asp Ile Ala Leu Met Lys Leu Gln Phe Pro Leu Thr Phe
        275                 280                 285

Ser Gly Thr Val Arg Pro Ile Cys Leu Pro Phe Phe Asp Glu Glu Leu
    290                 295                 300

Thr Pro Ala Thr Pro Leu Trp Ile Ile Gly Trp Gly Phe Thr Lys Gln
305                 310                 315                 320

Asn Gly Gly Lys Met Ser Asp Ile Leu Leu Gln Ala Ser Val Gln Val
                325                 330                 335

Ile Asp Ser Thr Arg Cys Asn Ala Asp Asp Ala Tyr Gln Gly Glu Val
                340                 345                 350

Thr Glu Lys Met Met Cys Ala Gly Ile Pro Glu Gly Gly Val Asp Thr
            355                 360                 365

Cys Gln Gly Asp Ser Gly Gly Pro Leu Met Tyr Gln Ser Asp Gln Trp
    370                 375                 380

His Val Val Gly Ile Val Ser Trp Gly Tyr Gly Cys Gly Gly Pro Ser
385                 390                 395                 400

Thr Pro Gly Val Tyr Thr Lys Val Ser Ala Tyr Leu Asn Trp Ile Tyr
                405                 410                 415

Asn Val Trp Lys Ala Glu Leu
                420

<210> SEQ ID NO 3
<211> LENGTH: 5
<212> TYPE: PRT
<213> ORGANISM: Unknown
<220> FEATURE:
<223> OTHER INFORMATION: cytokine receptor extracellular motif found in
      many species
<221> NAME/KEY: UNSURE
<222> LOCATION: (3)..(3)
<223> OTHER INFORMATION: "Xaa" at position 3 can be any amino acid.

<400> SEQUENCE: 3

Trp Ser Xaa Trp Ser
1               5
```

METHODS OF DIAGNOSING COLORECTAL CANCER, COMPOSITIONS, AND METHODS OF SCREENING FOR COLORECTAL CANCER MODULATORS

This application is a continuing application of U.S. application Ser. No. 09/525,993, filed on Mar. 15, 2000, which is a continuation-in-part of U.S. application Ser. No. 09/493,444 filed Jan. 28, 2000.

FIELD OF THE INVENTION

The invention relates to the identification of expression profiles and the nucleic acids involved in colorectal cancer, and to the use of such expression profiles and nucleic acids in diagnosis and prognosis of colorectal cancer. The invention further relates to methods for identifying and using candidate agents and/or targets which modulate colorectal cancer.

BACKGROUND OF THE INVENTION

Colorectal cancer is a significant cancer in Western populations. It develops as the result of a pathologic transformation of normal colon epithelium to an invasive cancer. There have been a number of recently characterized genetic alterations that have been implicated in colorectal cancer, including mutations in two classes of genes, tumor-suppressor genes and proto-oncogenes, with recent work suggesting that mutations in DNA repair genes may also be involved in tumorigenesis. For example, inactivating mutations of both alleles of the adenomatous polyposis coli (APC) gene, a tumor suppressor gene, appears to be one of the earliest events in colorectal cancer, and may even be the initiating event. Other genes implicated in colorectal cancer include the MCC gene, the p53 gene, the DCC (deleted in colorectal carcinoma) gene and other chromosome 18q genes, and genes in the TGF-β signalling pathway. For a review, see Molecular Biology of Colorectal Cancer, pp238–299, in Curr. Probl. Cancer, September/October 1997.

Imaging of colorectal cancer for diagnosis has been problematic and limited. In addition, dissemination of tumor cells (metastases) to locoregional lymph nodes is an important prognostic factor; five year survival rates drop from 80 percent in patients with no lymph node metastases to 45 to 50 percent in those patients who do have lymph node metastases. A recent report showed that micrometastases can be detected from lymph nodes using reverse transcriptase-PCR methods based on the presence of mRNA for carcinoembryonic antigen, which has previously been shown to be present in the vast majority of colorectal cancers but not in normal tissues. Liefers et al., New England J. of Med. 339(4):223 (1998).

Thus, methods that can be used for diagnosis and prognosis of colorectal cancer would be desirable. While academia and industry has made an effort to identify novel sequences, there has not been an equal effort exerted to identify the function of the novel sequences in disease states of concern, such as cancer. For example, databases show the sequence for accession numbers AA411502 and AF216312, and the later has been identified as a type II membrane serine protease, but there is no data correlating these sequences with a disease state. Further provided are methods that can be used to screen candidate bioactive agents for the ability to modulate colorectal cancer. Additionally, provided herein are molecular targets for therapeutic intervention in colorectal and other cancers.

SUMMARY OF THE INVENTION

The present invention provides methods for screening for compositions which modulate colorectal cancer. In one aspect, a method of screening drug candidates comprises providing a cell that expresses an expression profile gene or fragments thereof. Preferred embodiments of the expression profile gene as described herein include the sequence comprising CJA8 or a fragment thereof. The method further includes adding a drug candidate to the cell and determining the effect of the drug candidate on the expression of the expression profile gene.

In one embodiment, the method of screening drug candidates includes comparing the level of expression in the absence of the drug candidate to the level of expression in the presence of the drug candidate, wherein the concentration of the drug candidate can vary when present, and wherein the comparison can occur after addition or removal of the drug candidate. In a preferred embodiment, the cell expresses at least two expression profile genes. The profile genes may show an increase or decrease.

Also provided herein is a method of screening for a bioactive agent capable of binding to a colorectal cancer modulating protein (BCMP) or a fragment thereof, the method comprising combining the BCMP or fragment thereof and a candidate bioactive agent, and determining the binding of the candidate agent to the BCMP or fragment thereof. In a preferred embodiment, the BCMP is CJA8.

Further provided herein is a method for screening for a bioactive agent capable of modulating the bioactivity of a BCMP or a fragment thereof. In one embodiment, the method comprises combining the BCMP or fragment thereof and a candidate bioactive agent, and determining the effect of the candidate agent on the bioactivity of te BCMP or the fragment thereof. In a preferred embodiment, the BCMP is CJA8.

Also provided herein is a method of evaluating the effect of a candidate colorectal cancer drug comprising administering the drug to a transgenic animal expressing or overexpressing a BCMP or a fragment thereof, or an animal lacking a BCMP for example as a result of a gene knockout. In a preferred embodiment, the BCMP is CJA8.

Additionally, provided herein is a method of evaluating the effect of a candidate colorectal cancer drug comprising administering the drug to a patient and removing a cell sample from the patient. The expression profile of the cell is then determined. This method may further comprise comparing the expression profile to an expression profile of a healthy individual.

Furthermore, a method of diagnosing colorectal cancer is provided. The method comprises determining the expression of a gene which encodes CJA8 or a fragment thereof in a first tissue type of a first individual, and comparing this to the expression of the gene from a second unaffected individual. A difference in the expression indicates that the first individual has colorectal cancer.

In another aspect, the present invention provides an antibody which specifically binds to CJA8, or a fragment thereof. Preferably the antibody is a monoclonal antibody. The antibody can be a fragment of an antibody such as a single stranded antibody as further described herein, or can be conjugated to another molecule. In one embodiment, the antibody is a humanized antibody.

In one embodiment a method for screening for a bioactive agent capable of interfering with the binding of CJA8 or a fragment thereof and an antibody which binds to said CJA8 or fragment thereof is provided. In a preferred embodiment, the method comprises combining CJA8 or a fragment thereof, a candidate bioactive agent and an antibody which binds to said CJA8 or fragment thereof. The method further includes determining the binding of said CJA8 or fragment thereof and said antibody. Wherein there is a change in binding, an agent is identified as an interfering agent. The interfering agent can be an agonist or an antagonist. Preferably, the antibody as well as the agent inhibits colorectal cancer.

In one aspect of the invention, a method for inhibiting the activity of a colorectal cancer modulating protein are provided. The method comprises binding an inhibitor to the protein. In a preferred embodiment, the protein is CJA8.

In another aspect, the invention provides a method for neutralizing the effect of a colorectal cancer modulating protein. The method comprises contacting an agent specific for the protein with the protein in an amount sufficient to effect neutralization. In a preferred embodiment, the protein is CJA8.

In a further aspect, a method for treating or inhibiting colorectal cancer is provided. In one embodiment, the method comprises administering to a cell a composition comprising an antibody to CJA8 or a fragment thereof. In one embodiment, the antibody is conjugated to a therapeutic moiety. Such therapeutic moieties include a cytotoxic agent and a radioisotope. The method can be performed in vitro or in vivo, preferably in vivo to an individual. In a preferred embodiment the method of inhibiting colorectal cancer is provided to an individual with such cancer.

As described herein, methods of treating or inhibiting colorectal cancer can be performed by administering an inhibitor of CJA8 activity to a cell or individual. In one embodiment, a CJA8 inhibitor is an antisense molecule to a nucleic acid encoding CJA8.

Moreover, provided herein is a biochip comprising a nucleic acid segment which encodes CJA8, or a fragment thereof, wherein the biochip comprises fewer than 1000 nucleic acid probes. Preferably at least two nucleic acid segments are included.

Also provided herein are methods of eliciting an immune response in an individual. In one embodiment a method provided herein comprises administering to an individual a composition comprising CJA8 or a fragment thereof. In another aspect, said composition comprises a nucleic acid comprising a sequence encoding CJA8 or a fragment thereof.

Further provided herein are compositions capable of eliciting an immune response in an individual. In one embodiment, a composition provided herein comprises CJA8 or a fragment thereof and a pharmaceutically acceptable carrier. In another embodiment, said composition comprises a nucleic acid comprising a sequence encoding CJA8 or a fragment thereof and a pharmaceutically acceptable carrier.

Other aspects of the invention will become apparent to the skilled artisan by the following description of the invention.

DETAILED DESCRIPTION OF THE FIGURES

FIG. 1 (SEQ ID NO:1) shows an embodiment of a nucleic acid (mRNA) which includes a sequence which encodes a colorectal cancer protein provided herein, CJA8. The start and stop codons are shaded.

FIG. 2 (SEQ ID NO:2) shows an embodiment of an amino acid sequence of CJA8. A putative transmembrane region is shaded.

FIG. 3 shows the relative amount of expression of CJA8 in various samples of colorectal cancer tissue(dark bars) and many normal tissue types (light bars).

DETAILED DESCRIPTION OF THE INVENTION

The present invention provides novel methods for diagnosis and prognosis evaluation for colorectal cancer, as well as methods for screening for compositions which modulate colorectal cancer and compositions which bind to modulators of colorectal cancer. In one aspect, the expression levels of genes are determined in different patient samples for which either diagnosis or prognosis information is desired, to provide expression profiles. An expression profile of a particular sample is essentially a "fingerprint" of the state of the sample; while two states may have any particular gene similarly expressed, the evaluation of a number of genes simultaneously allows the generation of a gene expression profile that is unique to the state of the cell. That is, normal tissue may be distinguished from colorectal cancer tissue, and within colorectal cancer tissue, different prognosis states (good or poor long term survival prospects, for example) may be determined. By comparing expression profiles of colorectal cancer tissue in different states, information regarding which genes are important (including both up- and down-regulation of genes) in each of these states is obtained. The identification of sequences that are differentially expressed in colorectal cancer tissue versus normal colon tissue, as well as differential expression resulting in different prognostic outcomes, allows the use of this information in a number of ways. For example, the evaluation of a particular treatment regime may be evaluated: does a chemotherapeutic drug act to improve the long-term prognosis in a particular patient. Similarly, diagnosis may be done or confirmed by comparing patient samples with the known expression profiles. Furthermore, these gene expression profiles (or individual genes) allow screening of drug candidates with an eye to mimicking or altering a particular expression profile; for example, screening can be done for drugs that suppress the colorectal cancer expression profile or convert a poor prognosis profile to a better prognosis profile. This may be done by making biochips comprising sets of the important colorectal cancer genes, which can then be used in these screens. These methods can also be done on the protein basis; that is, protein expression levels of the colorectal cancer proteins can be evaluated for diagnostic and prognostic purposes or to screen candidate agents. In addition, the colorectal cancer nucleic acid sequences can be administered for gene therapy purposes, including the administration of antisense nucleic acids, or the colorectal cancer proteins (including antibodies and other modulators thereof) administered as therapeutic drugs.

Thus the present invention provides nucleic acid and protein sequences that are differentially expressed in colorectal cancer when compared to normal tissue. The differentially expressed sequences provided herein are termed "colorectal cancer sequences". As outlined below, colorectal cancer sequences include those that are up-regulated (i.e. expressed at a higher level) in colorectal cancer, as well as those that are down-regulated (i.e. expressed at a lower level) in colorectal cancer. In a preferred embodiment, the colorectal cancer sequences are from humans; however, as will be appreciated by those in the art, colorectal cancer sequences from other organisms may be useful in animal models of disease and drug evaluation; thus, other colorectal cancer sequences are provided, from vertebrates, including mammals, including rodents (rats, mice, hamsters, guinea pigs, etc.), primates, farm animals (including sheep, goats, pigs, cows, horses, etc). Colorectal cancer sequences from other organisms may be obtained using the techniques outlined below.

In a preferred embodiment, the colorectal cancer sequences are those of nucleic acids encoding CJA8 or fragments thereof. Preferably, the colorectal cancer sequences are those depicted in FIG. 1 (SEQ ID NO: 1), or fragments thereof. Preferably, the colorectal cancer sequences encode a protein having the amino acid sequence depicted in FIG. 2 (SEQ ID NO:2), or a fragment thereof. In a preferred embodiment, CJA8 has the sequence of a human type II membrane serine protease.

Colorectal cancer sequences can include both nucleic acid and amino acid sequences. In a preferred embodiment, the colorectal cancer sequences are recombinant nucleic acids. By the term "recombinant nucleic acid" herein is meant nucleic acid, originally formed in vitro, in general, by the manipulation of nucleic acid by polymerases and endonucleases, in a form not normally found in nature. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a colorectal cancer protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In a preferred embodiment, the colorectal cancer sequences are nucleic acids. As will be appreciated by those in the art and is more fully outlined below, colorectal cancer sequences are useful in a variety of applications, including diagnostic applications, which will detect naturally occurring nucleic acids, as well as screening applications; for example, biochips comprising nucleic acid probes to the colorectal cancer sequences can be generated. In the broadest sense, then, by "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramidate (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp169–176). Several nucleic acid analogs are described in Rawls, C & E News June 2,1997 page 35. All of these references are hereby expressly incorporated by reference. These modifications of the ribose-phosphate backbone may be done for a variety of reasons, for example to increase the stability and half-life of such molecules in physiological environments or as probes on a biochip.

As will be appreciated by those in the art, all of these nucleic acid analogs may find use in the present invention. In addition, mixtures of naturally occurring nucleic acids and analogs can be made; alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2–4° C. drop in Tm for an internal mismatch. With the non-ionic PNA backbone, the drop is closer to 7–9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be single stranded or double stranded, as specified, or contain portions of both double stranded or single stranded sequence. As will be appreciated by those in the art, the depiction of a single strand ("Watson") also defines the sequence of the other strand ("Crick"); thus the sequences described herein also includes the complement of the sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

A colorectal cancer sequence can be initially identified by substantial nucleic acid and/or amino acid sequence homology to the colorectal cancer sequences outlined herein. Such homology can be based upon the overall nucleic acid or amino acid sequence, and is generally determined as outlined below, using either homology programs or hybridization conditions.

The colorectal cancer sequences of the invention can be identified as follows. Samples of normal and tumor tissue are applied to biochips comprising nucleic acid probes. The samples are first microdissected, if applicable, and treated as is know in the art for the preparation of mRNA. Suitable biochips are commercially available, for example from Affymetrix. Gene expression profiles as described herein are generated, and the data analyzed.

In a preferred embodiment, the genes showing changes in expression as between normal and disease states are compared to genes expressed in other normal tissues, including, but not limited to lung, heart, brain, liver, colorectal, kidney, muscle, prostate, small intestine, large intestine, spleen, bone, and placenta. In a preferred embodiment, those genes identified during the colorectal cancer screen that are expressed in any significant amount in other tissues are removed from the profile, although in some embodiments, this is not necessary. That is, when screening for drugs, it is preferable that the target be disease specific, to minimize possible side effects.

In a preferred embodiment, colorectal cancer sequences are those that are up-regulated in colorectal cancer; that is, the expression of these genes is higher in colorectal carcinoma as compared to normal colon tissue. "Up-regulation" as used herein means at least about a 50% increase, preferably a two-fold change, more preferably at least about a three fold change, with at least about five-fold or higher being preferred. All accession numbers herein are for the GenBank sequence database and the sequences of the accession numbers are hereby expressly incorporated by reference. GenBank is known in the art, see, e.g., Benson, D A, et al., Nucleic Acids Research 26:1–7 (1998) and hftp://www.ncbi.nim.nih.gov/. In addition, these genes are found to be expressed in a limited amount or not at all in bladder, bone marrow, brain, breast, fibroblasts, heart, kidney, liver, lung, muscle, pancreas, prostate, skin, small intestine, spleen, stomach and testes.

In a preferred embodiment, the gene for CJA8 is upregulated in colon cancer tissue as compared with normal colon tissue.

In another embodiment, colorectal cancer sequences are those that are down-regulated in colorectal cancer; that is, the expression of these genes is lower in, for example, colorectal carcinoma as compared to normal colon tissue. "Down-regulation" as used herein means at least about a two-fold change, preferably at least about a three fold change, with at least about five-fold or higher being preferred.

Colorectal cancer proteins of the present invention may be classified as secreted proteins, transmembrane proteins or intracellular proteins. In a preferred embodiment the colorectal cancer protein is an intracellular protein. Intracellular proteins may be found in the cytoplasm and/or in the nucleus. Intracellular proteins are involved in all aspects of cellular function and replication (including, for example, signaling pathways); aberrant expression of such proteins results in unregulated or disregulated cellular processes. For example, many intracellular proteins have enzymatic activity such as protein kinase activity, protein phosphatase activity, protease activity, nucleotide cyclase activity, polymerase activity and the like. Intracellular proteins also serve as docking proteins that are involved in organizing complexes of proteins, or targeting proteins to various subcellular localizations, and are involved in maintaining the structural integrity of organelles.

An increasingly appreciated concept in characterizing intracellular proteins is the presence in the proteins of one or more motifs for which defined functions have been attributed. In addition to the highly conserved sequences found in the enzymatic domain of proteins, highly conserved sequences have been identified in proteins that are involved in protein-protein interaction. For example, Src-homology-2 (SH2) domains bind tyrosine-phosphorylated targets in a sequence dependent manner. PTB domains, which are distinct from SH2 domains, also bind tyrosine phosphorylated targets. SH3 domains bind to proline-rich targets. In addition, PH domains, tetratricopeptide repeats and WD domains to name only a few, have been shown to mediate protein-protein interactions. Some of these may also be involved in binding to phospholipids or other second messengers. As will be appreciated by one of ordinary skill in the art, these motifs can be identified on the basis of primary sequence; thus, an analysis of the sequence of proteins may provide insight into both the enzymatic potential of the molecule and/or molecules with which the protein may associate.

In a preferred embodiment, the colorectal cancer sequences are transmembrane proteins. Transmembrane proteins are molecules that span the phospholipid bilayer of a cell. They may have an intracellular domain, an extracellular domain, or both. The intracellular domains of such proteins may have a number of functions including those already described for intracellular proteins. For example, the intracellular domain may have enzymatic activity and/or may serve as a binding site for additional proteins. Frequently the intracellular domain of transmembrane proteins serves both roles. For example certain receptor tyrosine kinases have both protein kinase activity and SH2 domains. In addition, autophosphorylation of tyrosines on the receptor molecule itself, creates binding sites for additional SH2 domain containing proteins.

Transmembrane proteins may contain from one to many transmembrane domains. For example, receptor tyrosine kinases, certain cytokine receptors, receptor guanylyl cyclases and receptor serine/threonine protein kinases contain a single transmembrane domain. However, various other proteins including channels and adenylyl cyclases contain numerous transmembrane domains. Many important cell surface receptors are classified as "seven transmembrane domain" proteins, as they contain 7 membrane spanning regions. Important transmembrane protein receptors include, but are not limited to insulin receptor, insulin-like growth factor receptor, human growth hormone receptor, glucose transporters, transferrin receptor, epidermal growth factor receptor, low density lipoprotein receptor, epidermal growth factor receptor, leptin receptor, interleukin receptors, e.g. IL-1 receptor, IL-2 receptor, etc.

Characteristics of transmembrane domains include approximately 20 consecutive hydrophobic amino acids that may be followed by charged amino acids. Therefore, upon analysis of the amino acid sequence of a particular protein, the localization and number of transmembrane domains within the protein may be predicted.

The extracellular domains of transmembrane proteins are diverse; however, conserved motifs are found repeatedly among various extracellular domains. Conserved structure and/or functions have been ascribed to different extracellular motifs. For example, cytokine receptors are characterized by a cluster of cysteines and a WSXWS (W=tryptophan, S=serine, X=any amino acid; SEQ ID NO:3) motif. Immunoglobulin-like domains are highly conserved. Mucin-like domains may be involved in cell adhesion and leucine-rich repeats participate in protein-protein interactions.

Many extracellular domains are involved in binding to other molecules. In one aspect, extracellular domains are receptors. Factors that bind the receptor domain include circulating ligands, which may be peptides, proteins, or small molecules such as adenosine and the like. For example, growth factors such as EGF, FGF and PDGF are circulating growth factors that bind to their cognate receptors to initiate a variety of cellular responses. Other factors include cytokines, mitogenic factors, neurotrophic factors and the like. Extracellular domains also bind to cell-associated molecules. In this respect, they mediate cell-cell interactions. Cell-associated ligands can be tethered to the cell for example via a glycosylphosphatidylinositol (GPI) anchor, or may themselves be transmembrane proteins. Extracellular domains also associate with the extracellular matrix and contribute to the maintenance of the cell structure.

Colorectal cancer proteins that are transmembrane are particularly preferred in the present invention as they are good targets for immunotherapeutics, as are described herein. In addition, as outlined below, transmembrane proteins can be also useful in imaging modalities.

It will also be appreciated by those in the art that a transmembrane protein can be made soluble by removing transmembrane sequences, for example through recombinant methods. Furthermore, transmembrane proteins that have been made soluble can be made to be secreted through recombinant means by adding an appropriate signal sequence.

In a preferred embodiment, the colorectal cancer proteins are secreted proteins; the secretion of which can be either constitutive or regulated. These proteins have a signal peptide or signal sequence that targets the molecule to the secretory pathway. Secreted proteins are involved in numerous physiological events; by virtue of their circulating nature, they serve to transmit signals to various other cell types. The secreted protein may function in an autocrine manner (acting on the cell that secreted the factor), a paracrine manner (acting on cells in close proximity to the cell that secreted the factor) or an endocrine manner (acting on cells at a distance). Thus secreted molecules find use in modulating or altering numerous aspects of physiology. Colorectal cancer proteins that are secreted proteins are particularly preferred in the present invention as they serve as good targets for diagnostic markers, for example for blood tests.

A colorectal cancer sequence is initially identified by substantial nucleic acid and/or amino acid sequence homology to the colorectal cancer sequences outlined herein. Such homology can be based upon the overall nucleic acid or amino acid sequence, and is generally determined as outlined below, using either homology programs or hybridization conditions.

As used herein, a nucleic acid is a "colorectal cancer nucleic acid" if the overall homology of the nucleic acid sequence to the nucleic acid sequences encoding the amino acid sequences of the figures is preferably greater than about 75%, more preferably greater than about 80%, even more preferably greater than about 85% and most preferably greater than 90%. In some embodiments the homology will be as high as about 93 to 95 or 98%. Homology in this context means sequence similarity or identity, with identity being preferred. A preferred comparison for homology purposes is to compare the sequence containing sequencing errors to the correct sequence. This homology will be determined using standard techniques known in the art, including, but not limited to, the local homology algorithm of Smith & Waterman, Adv. Appl. Math. 2:482 (1981), by the homology alignment algorithm of Needleman & Wunsch, J. Mol. Biool. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387–395 (1984), preferably using the default settings, or by inspection.

In a preferred embodiment, the sequences which are used to determine sequence identity or similarity are selected from the sequences set forth in the figures, preferably those shown in FIG. 1 (SEQ ID NO:1) and fragments thereof. In one embodiment the sequences utilized herein are those set forth in the figures. In another embodiment, the sequences are naturally occurring allelic variants of the sequence set forth in the figures. In another embodiment, the sequences are sequenced variants as further described herein.

One example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403–410, (1990) and Karlin et al., PNAS USA 90:5873–5787 (1993). A particularly useful BLAST program is the WU-BLAST-2 program which was obtained from Altschul et al., Methods in Enzymology, 266: 460–480 (1996) [http://blast.wustl/edu/blast/ READ.html]. WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical with the nucleotide residues of FIG. 1 (SEQ ID NO:1). A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer nucleosides than those of the figures, it is understood that the percentage of homology will be determined based on the number of homologous nucleosides in relation to the total number of nucleosides. Thus, for example, homology of sequences shorter than those of the sequences identified herein and as discussed below, will be determined using the number of nucleosides in the shorter sequence.

In one embodiment, the nucleic acid homology is determined through hybridization studies. Thus, for example, nucleic acids which hybridize under high stringency to the nucleic acid sequences which encode the peptides identified in the figures, or their complements, are considered a colorectal cancer sequence. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology— Hybridization with Nucleic Acid Probes, "Overview of principles of hybridization and the strategy of nucleic acid assays" (1993). Generally, stringent conditions are selected to be about 5–10° C. lower than the thermal melting point (Tm) for the specific sequence at a defined ionic strength pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Maniatis and Ausubel, supra, and Tijssen, supra.

In addition, the colorectal cancer nucleic acid sequences of the invention are fragments of larger genes, i.e. they are nucleic acid segments. "Genes" in this context includes coding regions, non-coding regions, and mixtures of coding and non-coding regions. Accordingly, as will be appreciated by those in the art, using the sequences provided herein, additional sequences of the colorectal cancer genes can be obtained, using techniques well known in the art for cloning either longer sequences or the full length sequences; see Maniatis et al., and Ausubel, et al., supra, hereby expressly incorporated by reference.

Once the colorectal cancer nucleic acid is identified, it can be cloned and, if necessary, its constituent parts recombined to form the entire colorectal cancer nucleic acid. Once isolated from its natural source, e.g., contained within a plasmid or other vector or excised therefrom as a linear nucleic acid segment, the recombinant colorectal cancer nucleic acid can be further-used as a probe to identify and isolate other colorectal cancer nucleic acids, for example additional coding regions. It can also be used as a "precursor" nucleic acid to make modified or variant colorectal cancer nucleic acids and proteins.

The colorectal cancer nucleic acids of the present invention are used in several ways. In a first embodiment, nucleic acid probes to the colorectal cancer nucleic acids are made and attached to biochips to be used in screening and diagnostic methods, as outlined below, or for administration, for example for gene therapy and/or antisense applications. Alternatively, the colorectal cancer nucleic acids that include coding regions of colorectal cancer proteins can be put into expression vectors for the expression of colorectal cancer proteins, again either for screening purposes or for administration to a patient.

In a preferred embodiment, nucleic acid probes to colorectal cancer nucleic acids (both the nucleic acid sequences encoding peptides outlined in the figures and/or the complements thereof) are made. The nucleic acid probes attached to the biochip are designed to be substantially complementary to the colorectal cancer nucleic acids, i.e. the target sequence (either the target sequence of the sample or to other probe sequences, for example in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A nucleic acid probe is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. That is, generally whole genes are not used. In some embodiments, much longer nucleic acids can be used, up to hundreds of bases.

In a preferred embodiment, more than one probe per sequence is used, with either overlapping probes or probes to different sections of the target being used. That is, two, three, four or more probes, with three being preferred, are used to build in a redundancy for a particular target. The probes can be overlapping (i.e. have some sequence in common), or separate.

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined below. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably fluorescese. A preferred substrate is described in copending application entitled Reusable Low Fluorescent Plastic Biochip filed Mar. 15, 1999, herein incorporated by reference in its entirety.

Generally the substrate is planar, although as will be appreciated by those in the art, other configurations of substrates may be used as well. For example, the probes may be placed on the inside surface of a tube, for flow-through sample analysis to minimize sample volume. Similarly, the substrate may be flexible, such as a flexible foam, including closed cell foams made of particular plastics.

In a preferred embodiment, the surface of the biochip and the probe may be derivatized with chemical functional groups for subsequent attachment of the two. Thus, for example, the biochip is derivatized with a chemical functional group including, but not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo-or hetero-bifunctional linkers as are well known (see 1994 Pierce Chemical Company catalog, technical section on cross-linkers, pages 155–200, incorporated herein by reference). In addition, in some cases, additional linkers, such as alkyl groups (including substituted and heteroalkyl groups) may be used.

In this embodiment, the oligonucleotides are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affimetrix GeneChip™ technology.

In a preferred embodiment, colorectal cancer nucleic acids encoding colorectal cancer proteins are used to make a variety of expression vectors to express colorectal cancer proteins which can then be used in screening assays, as described below. The expression vectors may be either self-replicating extrachromosomal vectors or vectors which integrate into a host genome. Generally, these expression vectors include transcriptional and translational regulatory nucleic acid operably linked to the nucleic acid encoding the colorectal cancer protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the colorectal cancer protein; for example, transcriptional and translational regulatory nucleic acid sequences from Bacillus are preferably used to express the colorectal cancer protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The colorectal cancer proteins of the present invention are produced by culturing a host cell transformed with an expression vector containing nucleic acid encoding a colorectal cancer protein, under the appropriate conditions to induce or cause expression of the colorectal cancer protein. The conditions appropriate for colorectal cancer protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Drosophila melangaster* cells, *Saccharomyces cerevisiae* and other yeasts, *E. coli, Bacillus subtilis*, Sf9 cells, C129 cells, 293 cells, Neurospora, BHK, CHO, COS, HeLa cells, THP1 cell line (a macrophage cell line) and human cells and cell lines.

In a preferred embodiment, the colorectal cancer proteins are expressed in mammalian cells. Mammalian expression systems are also known in the art, and include retroviral systems. A preferred expression vector system is a retroviral vector system such as is generally described in PCT/US97/01019 and PCT/US97/01048, both of which are hereby expressly incorporated by reference. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter. Typically, transcription termination and polyadenylation sequences recognized by mammalian cells are regulatory regions located 3' to the translation stop codon and thus, together with the promoter elements, flank the coding sequence. Examples of transcription terminator and polyadenlytion signals include those derived form SV40.

The methods of introducing exogenous nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, colorectal cancer proteins are expressed in bacterial systems. Bacterial expression systems are well known in the art. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the colorectal cancer protein in bacteria. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways. These components are assembled into expression vectors.

Expression vectors for bacteria are well known in the art, and include vectors for *Bacillus subtilis, E. coli, Streptococcus cremoris*, and *Streptococcus lividans*, among others. The bacterial expression vectors are transformed into bacterial host cells using techniques well known in the art, such as calcium chloride treatment, electroporation, and others.

In one embodiment, colorectal cancer proteins are produced in insect cells. Expression vectors for the transformation of insect cells, and in particular, baculovirus-based expression vectors, are well known in the art.

In a preferred embodiment, colorectal cancer protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*.

The colorectal cancer protein may also be made as a fusion protein, using techniques well known in the art. Thus, for example, for the creation of monoclonal antibodies, if the desired epitope is small, the colorectal cancer protein may be fused to a carrier protein to form an immunogen.

Alternatively, the colorectal cancer protein may be made as a fusion protein to increase expression, or for other reasons. For example, when the colorectal cancer protein is a colorectal cancer peptide, the nucleic acid encoding the peptide may be linked to other nucleic acid for expression purposes.

In one embodiment, the colorectal cancer nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the colorectal cancer nucleic acids, proteins and antibodies at any position. For example, the label should be capable of producing, either directly or indirectly, a detectable signal. The detectable moiety may be a radioisotope, such as $^3H$, $^{14}C$, $^{32}P$, $^{35}S$, or $^{125}I$, a fluorescent or chemiluminescent compoun as fluorescein isothiocyanate, rhodamine, or luciferin, or an enzyme, such as alkaline phosphatase, beta-galactosidase or horseradish peroxidase. Any method known in the art for conjugating the antibody to the label may be employed, including those methods described by Hunter et al., *Nature*, 144:945 (1962); David et al., *Biochemistry*, 13:1014 (1974); Pain et al., *J. Immunol. Meth.*, 40:219 (1981); and Nygren, *J. Histochem, and Cytochem.*, 30:407 (1982).

Accordingly, the present invention also provides colorectal cancer protein sequences. A colorectal cancer protein of the present invention may be identified in several ways. "Protein" in this sense includes proteins, polypeptides, and peptides. As will be appreciated by those in the art, the nucleic acid sequences of the invention can be used to generate protein sequences. There are a variety of ways to do this, including cloning the entire gene and verifying its frame and amino acid sequence, or by comparing it to known sequences to search for homology to provide a frame, assuming the colorectal cancer protein has homology to some protein in the database being used. Generally, the nucleic acid sequences are input into a program that will search all three frames for homology. This is done in a preferred embodiment using the following NCBI Advanced BLAST parameters. The program is blastx or blastn. The database is nr. The input data is as "Sequence in FASTA format". The organism list is "none". The "expect" is 10; the filter is default. The "descriptions" is 500, the "alignments" is 500, and the "alignment view" is pairwise. The "Query Genetic Codes" is standard (1). The matrix is BLOSUM62; gap existence cost is 11, per residue gap cost is 1; and the lambda ratio is 0.85 default. This results in the generation of a putative protein sequence.

Also included within one embodiment of colorectal cancer proteins are amino acid variants of the naturally occurring sequences, as determined herein. Preferably, the variants are preferably greater than about 75% homologous to the wild-type sequence, more preferably greater than about 80%, even more preferably greater than about 85% and most preferably greater than 90%. In some embodiments the homology will be as high as about 93 to 95 or 98%. As for nucleic acids, homology in this context means sequence similarity or identity, with identity being preferred. This homology will be determined using standard techniques known in the art as are outlined above for the nucleic acid homologies.

Colorectal cancer proteins of the present invention may be shorter or longer than the wild type amino acid sequences. Thus, in a preferred embodiment, included within the definition of colorectal cancer proteins are portions or fragments of the wild type sequences herein. In addition, as outlined above, the colorectal cancer nucleic acids of the invention may be used to obtain additional coding regions, and thus additional protein sequence, using techniques known in the art.

In a preferred embodiment, the colorectal cancer proteins are derivative or variant colorectal cancer proteins as compared to the wild-type sequence. That is, as outlined more fully below, the derivative colorectal cancer peptide will contain at least one amino acid substitution, deletion or insertion, with amino acid substitutions being particularly preferred. The amino acid substitution, insertion or deletion may occur at any residue within the colorectal cancer peptide.

Also included in an embodiment of colorectal cancer proteins of the present invention are amino acid sequence variants. These variants fall into one or more of three classes: substitutional, insertional or deletional variants. These variants ordinarily are prepared by site specific mutagenesis of nucleotides in the DNA encoding the colorectal cancer protein, using cassette or PCR mutagenesis or other techniques well known in the art, to produce DNA encoding the variant, and thereafter expressing the DNA in recombinant cell culture as outlined above. However, variant colorectal cancer protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the colorectal cancer protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed colorectal cancer variants screened for the optimal combination of desired activity. Techniques for making substitution mutations at predetermined sites in DNA having a known sequence are well known, for example, M13 primer mutagenesis and PCR mutagenesis. Screening of the mutants is done using assays of colorectal cancer protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the colorectal cancer protein are desired, substitutions are generally made in accordance with the following chart:

CHART 1

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart 1. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue, although variants also are selected to modify the characteristics of the colorectal cancer proteins as needed. Alternatively, the variant may be designed such that the biological activity of the colorectal cancer protein is altered. For example, glycosylation sites may be altered or removed.

Covalent modifications of colorectal cancer polypeptides are included within the scope of this invention. One type of covalent modification includes reacting targeted amino acid residues of a colorectal cancer polypeptide with an organic derivatizing agent that is capable of reacting with selected side chains or the N-or C-terminal residues of a colorectal cancer polypeptide. Derivatization with bifunctional agents is useful, for instance, for crosslinking colorectal cancer to a water-insoluble support matrix or surface for use in the method for purifying anti-colorectal cancer antibodies or screening assays, as is more fully described below. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl, threonyl or tyrosyl residues, methylation of the α-amino groups of lysine, arginine, and histidine side chains [T. E. Creighton, Proteins: Structure and Molecular Properties, W.H. Freeman & Co., San Francisco, pp. 79–86 (1983)], acetylation of the N-terminal amine, and amidation of any C-terminal carboxyl group.

Another type of covalent modification of the colorectal cancer polypeptide included within the scope of this invention comprises altering the native glycosylation pattern of the polypeptide. "Altering the native glycosylation pattern" is intended for purposes herein to mean deleting one or more carbohydrate moieties found in native sequence colorectal cancer polypeptide, and/or adding one or more glycosylation sites that are not present in the native sequence colorectal cancer polypeptide.

Addition of glycosylation sites to colorectal cancer polypeptides may be accomplished by altering the amino acid sequence thereof. The alteration may be made, for example, by the addition of, or substitution by, one or more serine or threonine residues to the native sequence colorectal cancer polypeptide (for O-linked glycosylation sites). The colorectal cancer amino acid sequence may optionally be altered through changes at the DNA level, particularly by mutating the DNA encoding the colorectal cancer polypeptide at preselected bases such that codons are generated that will translate into the desired amino acids.

Another means of increasing the number of carbohydrate moieties on the colorectal cancer polypeptide is by chemical or enzymatic coupling of glycosides to the polypeptide. Such methods are described in the art, e.g., in WO 87/05330 published Sep. 11, 1987, and in Aplin and Wriston, colorectal cancer Crit. Rev. Biochem., pp. 259–306 (1981).

Removal of carbohydrate moieties present on the colorectal cancer polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Thotakura et al., Meth. Enzymol., 138:350 (1987).

Another type of covalent modification of colorectal cancer protein comprises linking the colorectal cancer polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Colorectal cancer polypeptides of the present invention may also be modified in a way to form chimeric molecules comprising a colorectal cancer polypeptide fused to another, heterologous polypeptide or amino acid sequence. In one embodiment, such a chimeric molecule comprises a fusion of a colorectal cancer polypeptide with a tag polypeptide which provides an epitope to which an anti-tag antibody can selectively bind. The epitope tag is generally placed at the amino-or carboxyl-terminus of the colorectal cancer polypeptide. The presence of such epitope-tagged forms of a colorectal cancer polypeptide can be detected using an antibody against the tag polypeptide. Also, provision of the epitope tag enables the colorectal cancer polypeptide to be readily purified by affinity purification using an anti-tag antibody or another type of affinity matrix that binds to the epitope tag. In an alternative embodiment, the chimeric molecule may comprise a fusion of a colorectal cancer polypeptide with an immunoglobulin or a particular region of an immunoglobulin. For a bivalent form of the chimeric molecule, such a fusion could be to the Fc region of an IgG molecule.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159–2165 (1988)]; the c-myc tag and the 8F9, 3 7, 6E10, G4, B7 and 9E10 antibodies thereto [Evan et al., Molecular and Cellular Biology, 5:3610' (1985)]; and the Herpes Simplex virus glycoprotein D (gD) tag and its antibody [Paborsky et al., Protein Engineering, 3(6):547–553 (1990)]. Other tag polypeptides include the Flag-peptide [Hopp et al., BioTechnology, 6:1204–1210 (1988)]; the KT3 epitope peptide [Martin et al., Science, 255:192–194 (1992)]; tubulin epitope peptide [Skinner et al., J. Biol. Chem., 266:15163–15166 (1991)]; and the T7 gene 10 protein peptide tag [Lutz-Freyermuth et al., Proc. Natl. Acad. Sci. USA, 87:6393–6397 (1990)].

Also included with the definition of colorectal cancer protein in one embodiment are other colorectal cancer proteins of the colorectal cancer family, and colorectal cancer proteins from other organisms, which are cloned and expressed as outlined below. Thus, probe or degenerate polymerase chain reaction (PCR) primer sequences may be used to find other related colorectal cancer proteins from humans or other organisms. As will be appreciated by those in the art, particularly useful probe and/or PCR primer sequences include the unique areas of the colorectal cancer nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art.

In addition, as is outlined herein, colorectal cancer proteins can be made that are longer than those depicted in the figures, for example, by the elucidation of additional sequences, the addition of epitope or purification tags, the addition of other fusion sequences, etc.

Colorectal cancer proteins may also be identified as being encoded by colorectal cancer nucleic acids.

Thus, colorectal cancer proteins are encoded by nucleic acids that will hybridize to the sequences of the sequence listings, or their complements, as outlined herein.

In a preferred embodiment, when the colorectal cancer protein is to be used to generate antibodies, for example for immunotherapy, the colorectal cancer protein should share at least one epitope or determinant with the full length protein. By "epitope" or "determinant" herein is meant a portion of a protein which will generate and/or bind an antibody or T-cell receptor in the context of MHC. Thus, in most instances, antibodies made to a smaller colorectal cancer protein will be able to bind to the full length protein. In a preferred embodiment, the epitope is unique; that is, antibodies generated to a unique epitope show little or no cross-reactivity.

In one embodiment, the term "antibody" includes antibody fragments, as are known in the art, including Fab, Fab$_2$, single chain antibodies (Fv for example), chimeric antibodies, etc., either produced by the modification of whole antibodies or those synthesized de novo using recombinant DNA technologies.

Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the CJA8 or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The antibodies may, alternatively, be monoclonal antibodies. Monoclonal antibodies may be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include the CJA8 polypeptide or fragment thereof or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, Monoclonal Antibodies: Principles and Practice, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In one embodiment, the antibodies are bispecific antibodies. Bispecific antibodies are monoclonal, preferably human or humanized, antibodies that have binding specificities for at least two different antigens. In the present case, one of the binding specificities is for the CJA8 or a fragment thereof, the other one is for any other antigen, and preferably for a cell-surface protein or receptor or receptor subunit, preferably one that is tumor specific.

In a preferred embodiment, the antibodies to colorectal cancer are capable of reducing or eliminating the biological function of colorectal cancer, as is described below. That is, the addition of anti-colorectal cancer antibodies (either polyclonal or preferably monoclonal) to colorectal cancer (or cells containing colorectal cancer) may reduce or eliminate the colorectal cancer activity. Generally, at least a 25% decrease in activity is preferred, with at least about 50% being particularly preferred and about a 95–100% decrease being especially preferred.

In a preferred embodiment the antibodies to the colorectal cancer proteins are humanized antibodies. Humanized forms of non-human (e.g., murine) antibodies are chimeric molecules of immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. OP. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boemer et al., *J. Immunol.*, 147(1):86–95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994); Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

By immunotherapy is meant treatment of colorectal cancer with an antibody raised against colorectal cancer proteins. As used herein, immunotherapy can be passive or active. Passive immunotherapy as defined herein is the passive transfer of antibody to a recipient (patient). Active immunization is the induction of antibody and/or T-cell responses in a recipient (patient). Induction of an immune response is the result of providing the recipient with an antigen to which antibodies are raised. As appreciated by one of ordinary skill in the art, the antigen may be provided by injecting a polypeptide against which antibodies are desired to be raised into a recipient, or contacting the recipient with a nucleic acid capable of expressing the antigen and under conditions for expression of the antigen.

In a preferred embodiment the colorectal cancer proteins against which antibodies are raised are secreted proteins as described above. Without being bound by theory, antibodies used for treatment, bind and prevent the secreted protein from binding to its receptor, thereby inactivating the secreted colorectal cancer protein.

In another preferred embodiment, the colorectal cancer protein to which antibodies are raised is a transmembrane protein. Without being bound by theory, antibodies used for treatment, bind the extracellular domain of the colorectal cancer protein and prevent it from binding to other proteins, such as circulating ligands or cell-associated molecules. The antibody may cause down-regulation of the transmembrane colorectal cancer protein. As will be appreciated by one of ordinary skill in the art, the antibody may be a competitive, non-competitive or uncompetitive inhibitor of protein binding to the extracellular domain of the colorectal cancer protein. The antibody is also an antagonist of the colorectal cancer protein. Further, the antibody prevents activation of the transmembrane colorectal cancer protein. In one aspect, when the antibody prevents the binding of other molecules to the colorectal cancer protein, the antibody prevents growth of the cell. The antibody also sensitizes the cell to cytotoxic agents, including, but not limited to TNF-α, TNF-β, IL-1, INF-γ and IL-2, or chemotherapeutic agents including 5FU, vinblastine, actinomycin D, cisplatin, methotrexate, and the like. In some instances the antibody belongs to a sub-type that activates serum complement when complexed with the transmembrane protein thereby mediating cytotoxicity. Thus, colorectal cancer is treated by administering to a patient antibodies directed against the transmembrane colorectal cancer protein.

In another preferred embodiment, the antibody is conjugated to a therapeutic moiety. In one aspect the therapeutic moiety is a small molecule that modulates the activity of the colorectal cancer protein. In another aspect the therapeutic moiety modulates the activity of molecules associated with or in close proximity to the colorectal cancer protein. The therapeutic moiety may inhibit enzymatic activity such as protease or protein kinase activity associated with colorectal cancer.

In a preferred embodiment, the therapeutic moiety may also be a cytotoxic agent. In this method, targeting the cytotoxic agent to tumor tissue or cells, results in a reduction in the number of afflicted cells, thereby reducing symptoms associated with colorectal cancer. Cytotoxic agents are numerous and varied and include, but are not limited to, cytotoxic drugs or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies raised against colorectal cancer proteins, or binding of a radionuclide to a chelating agent that has been covalently attached to the antibody. Targeting the therapeutic moiety to transmembrane colorectal cancer proteins not only serves to increase the local concentration of therapeutic moiety in the colorectal cancer afflicted area, but also serves to reduce deleterious side effects that may be associated with the therapeutic moiety.

In another preferred embodiment, the PC protein against which the antibodies are raised is an intracellular protein. In this case, the antibody may be conjugated to a protein which facilitates entry into the cell. In one case, the antibody enters the cell by endocytosis. In another embodiment, a nucleic acid encoding the antibody is administered to the individual or cell. Moreover, wherein the PC protein can be targeted within a cell, i.e., the nucleus, an antibody thereto contains a signal for that target localization, i.e., a nuclear localization signal.

The colorectal cancer antibodies of the invention specifically bind to colorectal cancer proteins. By "specifically bind" herein is meant that the antibodies bind to the protein with a binding constant in the range of at least $10^{-4}$–$10^{-6}$ $M^{-1}$, with a preferred range being $10^{-7}$–$10^{-9}$ $M^{-1}$.

In a preferred embodiment, the colorectal cancer protein is purified or isolated after expression. Colorectal cancer proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing.

For example, the colorectal cancer protein may be purified using a standard anti-colorectal cancer antibody column. Ultrafiltration and diafiltration techniques, in conjunction with protein concentration, are also useful. For general guidance in suitable purification techniques, see Scopes, R., Protein Purification, Springer-Verlag, N.Y. (1982). The degree of purification necessary will vary depending on the use of the colorectal cancer protein. In some instances no purification will be necessary.

Once expressed and purified if necessary, the colorectal cancer proteins and nucleic acids are useful in a number of applications.

In one aspect, the expression levels of genes are determined for different cellular states in the colorectal cancer phenotype; that is, the expression levels of genes in normal colon tissue and in colorectal cancer tissue (and in some cases, for varying severities of colorectal cancer that relate to prognosis, as outlined below) are evaluated to provide expression profiles. An expression profile of a particular cell state or point of development is essentially a "fingerprint" of the state; while two states may have any particular gene similarly expressed, the evaluation of a number of genes simultaneously allows the generation of a gene expression profile that is unique to the state of the cell. By comparing expression profiles of cells in different states, information regarding which genes are important (including both up- and down-regulation of genes) in each of these states is obtained. Then, diagnosis may be done or confirmed: does tissue from a particular patient have the gene expression profile of normal or colorectal cancer tissue.

"Differential expression," or grammatical equivalents as used herein, refers to both qualitative as well as quantitative differences in the genes' temporal and/or cellular expression patterns within and among the cells. Thus, a colorectal cancer gene can qualitatively have its expression altered, including an activation or inactivation, in, for example, normal versus colorectal cancer tissue. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart, Nature Biotechnology, 14:1675–1680 (1996), hereby expressly incorporated by reference. Other techniques include, but are not limited to, quantitative reverse transcriptase PCR, Northern analysis and RNase protection. As outlined above, preferably the change in expression (i.e. upregulation or downregulation) is at least about 50%, more preferably at least about 100%, more preferably at least about 150%, more preferably, at least about 200%, with from 300 to at least 1000% being especially preferred.

As will be appreciated by those in the art, this may be done by evaluation at either the gene transcript, or the protein level; that is, the amount of gene expression may be monitored using nucleic acid probes to the DNA or RNA equivalent of the gene transcript, and the quantification of gene expression levels, or, alternatively, the final gene product itself (protein) can be monitored, for example through the use of antibodies to the colorectal cancer protein and standard immunoassays (ELISAs,etc.) or other techniques, including mass spectroscopy assays, 2D gel electrophoresis assays, etc. Thus, the proteins corresponding to colorectal cancer genes, i.e. those identified as being important in a colorectal cancer phenotype, can be evaluated in a colorectal cancer diagnostic test.

In a preferred embodiment, gene expression monitoring is done and a number of genes, i.e. an expression profile, is monitored simultaneously, although multiple protein expression monitoring can be done as well. Similarly, these assays may be done on an individual basis as well.

In this embodiment, the colorectal cancer nucleic acid probes are attached to biochips as outlined herein for the detection and quantification of colorectal cancer sequences in a particular cell. The assays are further described below in the example.

In a preferred embodiment nucleic acids encoding the colorectal cancer protein are detected. Although DNA or RNA encoding the colorectal cancer protein may be detected, of particular interest are methods wherein the mRNA encoding a colorectal cancer protein is detected. The presence of mRNA in a sample is an indication that the colorectal cancer gene has been transcribed to form the mRNA, and suggests that the protein is expressed. Probes to detect the mRNA can be any nucleotide/deoxynucleotide probe that is complementary to and base pairs with the mRNA and includes but is not limited to oligonucleotides, cDNA or RNA. Probes also should contain a detectable label, as defined herein. In one method the mRNA is detected after immobilizing the nucleic acid to be examined on a solid support such as nylon membranes and hybridizing the probe with the sample. Following washing to remove the non-specifically bound probe, the label is detected. In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding a colorectal cancer protein is detected by binding the digoxygenin with an anti-digoxygenin secondary antibody and developed with nitro blue tetrazolium and 5-bromo-4-chloro-3-indoyl phosphate.

In a preferred embodiment, any of the three classes of proteins as described herein (secreted, transmembrane or intracellular proteins) are used in diagnostic assays. The colorectal cancer proteins, antibodies, nucleic acids, modified proteins and cells containing colorectal cancer sequences are used in diagnostic assays. This can be done on an individual gene or corresponding polypeptide level. In a preferred embodiment, the expression profiles are used, preferably in conjunction with high throughput screening techniques to allow monitoring for expression profile genes and/or corresponding polypeptides.

As described and defined herein, colorectal cancer proteins, including intracellular, transmembrane or secreted proteins, find use as markers of colorectal cancer. Detection of these proteins in putative colorectal cancer tissue of patients allows for a determination or diagnosis of colorectal cancer. Numerous methods known to those of ordinary skill in the art find use in detecting colorectal cancer. In one embodiment, antibodies are used to detect colorectal cancer proteins. A preferred method separates proteins from a sample or patient by electrophoresis on a gel (typically a denaturing and reducing protein gel, but may be any other type of gel including isoelectric focusing gels and the like). Following separation of proteins, the colorectal cancer protein is detected by immunoblotting with antibodies raised against the colorectal cancer protein. Methods of immunoblotting are well known to those of ordinary skill in the art.

In another preferred method, antibodies to the colorectal cancer protein find use in in situ imaging techniques. In this method cells are contacted with from one to many antibodies to the colorectal cancer protein(s). Following washing to remove non-specific antibody binding, the presence of the antibody or antibodies is detected. In one embodiment the antibody is detected by incubating with a secondary antibody that contains a detectable label. In another method the primary antibody to the colorectal cancer protein(s) contains a detectable label. In another preferred embodiment each one of multiple primary antibodies contains a distinct and detectable label. This method finds particular use in simultaneous screening for a plurality of colorectal cancer proteins. As will be appreciated by one of ordinary skill in the art, numerous other histological imaging techniques are useful in the invention.

In a preferred embodiment the label is detected in a fluorometer which has the ability to detect and distinguish emissions of different wavelengths. In addition, a fluorescence activated cell sorter (FACS) can be used in the method.

In another preferred embodiment, antibodies find use in diagnosing colorectal cancer from blood samples. As previously described, certain colorectal cancer proteins are secreted/circulating molecules. Blood samples, therefore, are useful as samples to be probed or tested for the presence of secreted colorectal cancer proteins. Antibodies can be used to detect the colorectal cancer by any of the previously described immunoassay techniques including ELISA, immunoblotting (Western blotting), immunoprecipitation, BIACORE technology and the like, as will be appreciated by one of ordinary skill in the art.

In a preferred embodiment, in situ hybridization of labeled colorectal cancer nucleic acid probes to tissue arrays is done. For example, arrays of tissue samples, including colorectal cancer tissue and/or normal tissue, are made. In situ hybridization as is known in the art can then be done.

It is understood that when comparing the fingerprints between an individual and a standard, the skilled artisan can make a diagnosis as well as a prognosis. It is further understood that the genes which indicate the diagnosis may differ from those which indicate the prognosis.

In a preferred embodiment, the colorectal cancer proteins, antibodies, nucleic acids, modified proteins and cells containing colorectal cancer sequences are used in prognosis assays. As above, gene expression profiles can be generated that correlate to colorectal cancer severity, in terms of long term prognosis. Again, this may be done on either a protein or gene level, with the use of genes being preferred. As above, the colorectal cancer probes are attached to biochips for the detection and quantification of colorectal cancer sequences in a tissue or patient. The assays proceed as outlined for diagnosis.

In a preferred embodiment, any of the three classes of proteins as described herein are used in drug screening assays. The colorectal cancer proteins, antibodies, nucleic acids, modified proteins and cells containing colorectal cancer sequences are used in drug screening assays or by evaluating the effect of drug candidates on a "gene expression profile" or expression profile of polypeptides. In a preferred embodiment, the expression profiles are used, preferably in conjunction with high throughput screening techniques to allow monitoring for expression profile genes after treatment with a candidate agent, Zlokamik, et al., Science 279, 84–8 (1998), Heid, 1996 #69.

In a preferred embodiment, the colorectal cancer proteins, antibodies, nucleic acids, modified proteins and cells containing the native or modified colorectal cancer proteins are used in screening assays. That is, the present invention provides novel methods for screening for compositions which modulate the colorectal cancer phenotype. As above, this can be done on an individual gene level or by evaluating the effect of drug candidates on a "gene expression profile". In a preferred embodiment, the expression profiles are used, preferably in conjunction with high throughput screening techniques to allow monitoring for expression profile genes after treatment with a candidate agent, see Zlokamik, supra.

Having identified the colorectal cancer genes herein, a variety of assays may be executed. In a preferred embodiment, assays may be run on an individual gene or protein level. That is, having identified a particular gene as up regulated in colorectal cancer, candidate bioactive agents may be screened to modulate this gene's response; preferably to down regulate the gene, although in some circumstances to up regulate the gene. "Modulation" thus includes both an increase and a decrease in gene expression. The preferred amount of modulation will depend on the original change of the gene expression in normal versus tumor tissue, with changes of at least 10%, preferably 50%, more preferably 100–300%, and in some embodiments 300–1000% or greater. Thus, if a gene exhibits a 4 fold increase in tumor compared to normal tissue, a decrease of about four fold is desired; a 10 fold decrease in tumor compared to normal tissue gives a 10 fold increase in expression for a candidate agent is desired.

As will be appreciated by those in the art, this may be done by evaluation at either the gene or the protein level; that is, the amount of gene expression may be monitored using nucleic acid probes and the quantification of gene expression levels, or, alternatively, the gene product itself can be monitored, for example through the use of antibodies to the colorectal cancer protein and standard immunoassays.

In a preferred embodiment, gene expression monitoring is done and a number of genes, i.e. an expression profile, is monitored simultaneously, although multiple protein expression monitoring can be done as well.

In this embodiment, the colorectal cancer nucleic acid probes are attached to biochips as outlined herein for the detection and quantification of colorectal cancer sequences in a particular cell. The assays are further described below.

Generally, in a preferred embodiment, a candidate bioactive agent is added to the cells prior to analysis. Moreover, screens are provided to identify a candidate bioactive agent which modulates colorectal cancer, modulates colorectal cancer proteins, binds to a colorectal cancer protein, or interferes between the binding of a colorectal cancer protein and an antibody.

The term "candidate bioactive agent" or "drug candidate" or grammatical equivalents as used herein describes any molecule, e.g., protein, oligopeptide, small organic molecule, polysaccharide, polynucleotide, etc., to be tested for bioactive agents that are capable of directly or indirectly altering the colorectal cancer phenotype or the expression of a colorectal cancer sequence, including both nucleic acid sequences and protein sequences. In preferred embodiments, the bioactive agents modulate the expression profiles, or expression profile nucleic acids or proteins provided herein. In a particularly preferred embodiment, the candidate agent suppresses a colorectal cancer phenotype, for example to a normal colon tissue fingerprint. Similarly, the candidate agent preferably suppresses a severe colorectal cancer phenotype. Generally a plurality of assay mixtures are run in parallel with different agent concentrations to obtain a differential response to the various concentrations. Typically, one of these concentrations serves as a negative control, i.e., at zero concentration or below the level of detection.

In one aspect, a candidate agent will neutralize the effect of a CRC protein. By "neutralize" is meant that activity of a protein is either inhibited or counter acted against so as to have substantially no effect on a cell.

Candidate agents encompass numerous chemical classes, though typically they are organic molecules, preferably small organic compounds having a molecular weight of more than 100 and less than about 2,500 daltons. Preferred small molecules are less than 2000, or less than 1500 or less than 1000 or less than 500 D. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and norleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eucaryotic proteins may be made for screening in the methods of the invention. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids, as defined above.

As described above generally for proteins, nucleic acid candidate bioactive agents may be naturally occurring nucleic acids, random nucleic acids, or "biased" random nucleic acids. For example, digests of procaryotic or eucaryotic genomes may be used as is outlined above for proteins.

In a preferred embodiment, the candidate bioactive agents are organic chemical moieties, a wide variety of which are available in the literature.

After the candidate agent has been added and the cells allowed to incubate for some period of time, the sample containing the target sequences to be analyzed is added to the biochip. If required, the target sequence is prepared using known techniques. For example, the sample may be treated to lyse the cells, using known lysis buffers, electroporation, etc., with purification and/or amplification such as PCR occurring as needed, as will be appreciated by those in the art. For example, an in vitro transcription with labels covalently attached to the nucleosides is done. Generally, the nucleic acids are labeled with biotin-FITC or PE, or with cy3 or cy5.

In a preferred embodiment, the target sequence is labeled with, for example, a fluorescent, a chemiluminescent, a chemical, or a radioactive signal, to provide a means of detecting the target sequence's specific binding to a probe. The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. As known in the art, unbound labeled streptavidin is removed prior to analysis.

As will be appreciated by those in the art, these assays can be direct hybridization assays or can comprise "sandwich assays", which include the use of multiple probes, as is generally outlined in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference. In this embodiment, in general, the target nucleic acid is prepared as outlined above, and then added to the biochip comprising a plurality of nucleic acid probes, under conditions that allow the formation of a hybridization complex.

A variety of hybridization conditions may be used in the present invention, including high, moderate and low stringency conditions as outlined above. The assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

The reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

Once the assay is run, the data is analyzed to determine the expression levels, and changes in expression levels as between states, of individual genes, forming a gene expression profile.

The screens are done to identify drugs or bioactive agents that modulate the colorectal cancer phenotype. Specifically, there are several types of screens that can be run. A preferred embodiment is in the screening of candidate agents that can induce or suppress a particular expression profile, thus preferably generating the associated phenotype. That is, candidate agents that can mimic or produce an expression profile in colorectal cancer similar to the expression profile of normal colon tissue is expected to result in a suppression of the colorectal cancer phenotype. Thus, in this embodiment, mimicking an expression profile, or changing one profile to another, is the goal.

In a preferred embodiment, as for the diagnosis and prognosis applications, having identified the colorectal cancer genes important in any one state, screens can be run to alter the expression of the genes individually. That is, screening for modulation of regulation of expression of a single gene can be done; that is, rather than try to mimic all or part of an expression profile, screening for regulation of individual genes can be done. Thus, for example, particularly in the case of target genes whose presence or absence is unique between two states, screening is done for modulators of the target gene expression.

In a preferred embodiment, screening is done to alter the biological function of the expression product of the colorectal cancer gene. Again, having identified the importance of a gene in a particular state, screening for agents that bind and/or modulate the biological activity of the gene product can be run as is more fully outlined below.

Thus, screening of candidate agents that modulate the colorectal cancer phenotype either at the gene expression level or the protein level can be done.

In addition screens can be done for novel genes that are induced in response to a candidate agent. After identifying a candidate agent based upon its ability to suppress a colorectal cancer expression pattern leading to a normal expression pattern, or modulate a single colorectal cancer gene expression profile so as to mimic the expression of the gene from normal tissue, a screen as described above can be performed to identify genes that are specifically modulated in response to the agent. Comparing expression profiles between normal tissue and agent treated colorectal cancer tissue reveals genes that are not expressed in normal colon tissue or colorectal cancer tissue, but are expressed in agent treated tissue. These agent specific sequences can be identified and used by any of the methods described herein for colorectal cancer genes or proteins. In particular these sequences and the proteins they encode find use in marking or identifying agent treated cells. In addition, antibodies can be raised against the agent induced proteins and used to target novel therapeutics to the treated colorectal cancer tissue sample.

Thus, in one embodiment, a candidate agent is administered to a population of colorectal cancer cells, that thus has an associated colorectal cancer expression profile. By "administration" or "contacting" herein is meant that the candidate agent is added to the cells in such a manner as to allow the agent to act upon the cell, whether by uptake and intracellular action, or by action at the cell surface. In some embodiments, nucleic acid encoding a proteinaceous candidate agent (i.e. a peptide) may be put into a viral construct such as a retroviral construct and added to the cell, such that expression of the peptide agent is accomplished; see PCT US97/01019, hereby expressly incorporated by reference.

Once the candidate agent has been administered to the cells, the cells can be washed if desired and are allowed to incubate under preferably physiological conditions for some period of time. The cells are then harvested and a new gene expression profile is generated, as outlined herein.

Thus, for example, colorectal cancer tissue may be screened for agents that reduce or suppress the colorectal cancer phenotype. A change in at least one gene of the expression profile indicates that the agent has an effect on colorectal cancer activity. By defining such a signature for the colorectal cancer phenotype, screens for new drugs that alter the phenotype can be devised. With this approach, the drug target need not be known and need not be represented in the original expression screening platform, nor does the level of transcript for the target protein need to change.

In a preferred embodiment, as outlined above, screens may be done on individual genes and gene products (proteins). That is, having identified a particular colorectal cancer gene as important in a particular state, screening of modulators of either the expression of the gene or the gene product itself can be done. The gene products of colorectal cancer genes are sometimes referred to herein as "colorectal cancer proteins" or "colorectal cancer modulating proteins" or "BCMP". Additionally, "modulator" and "modulating" proteins are sometimes used interchangeably herein. In one embodiment, the colorectal cancer protein is termed CJA8. CJA8 sequences can be identified as described herein for colorectal cancer sequences. In one embodiment, CJA8 protein sequences are as depicted in FIG. 2 (SEQ ID NO:2). The colorectal cancer protein may be a fragment, or alternatively, be the full length protein to the fragment shown herein. Preferably, the colorectal cancer protein is a fragment. In a preferred embodiment, the amino acid sequence which is used to determine sequence identity or similarity is that depicted in FIG. 2. In another embodiment, the sequences are naturally occurring alelic variants of a protein having the sequence depicted in FIG. 2. In another embodiment, the sequences are sequence variants as further described herein.

Preferably, the colorectal cancer protein is a fragment of approximately 14 to 24 amino acids long. More preferably the fragment is a soluble fragment. Preferably, the fragment includes a non-transmembrane region. In a preferred embodiment, the fragment has an N-terminal Cys to aid in solubility. In one embodiment, the c-terminus of the fragment is kept as a free acid and the n-terminus is a free amine to aid in coupling, i.e., to cysteine. Preferably, the fragment of approximately 14 to 24 amino acids long. More preferably the fragment is a soluble fragment. In another embodiment, a CJA8 fragment has at least one CJA8 bioactivity as defined below.

In one embodiment the colorectal cancer proteins are conjugated to an immunogenic agent as discussed herein. In one embodiment the colorectal cancer protein is conjugated to BSA. In a preferred embodiment, as outlined above, screens may be done on individual genes and gene products (proteins). That is, having identified a particular colorectal cancer gene as important in a particular state, screening of modulators of either the expression of the gene or the gene product itself can be done. The gene products of colorectal cancer genes are sometimes referred to herein as "colorectal cancer proteins" or "colorectal cancer modulating proteins" or "BCMP". Additionally, "modulator" and "modulating" proteins are sometimes used interchangeably herein. In one embodiment, the colorectal cancer protein is termed CJA8. CJA8 sequences can be identified as described herein for colorectal cancer sequences. In one embodiment, CJA8 protein sequences are as depicted in FIG. 2 (SEQ ID NO:2). The colorectal cancer protein may be a fragment, or alternatively, be the full length protein to the fragment shown herein. Preferably, the colorectal cancer protein is a fragment. In a preferred embodiment, the amino acid sequence which is used to determine sequence identity or similarity is that depicted in FIG. 2. In another embodiment, the sequences are naturally occurring alelic variants of a protein having the sequence depicted in FIG. 2. In another embodiment, the sequences are sequence variants as further described herein. Thus, in a preferred embodiment, screening for modulators of expression of specific genes can be done. This will be done as outlined above, but in general the expression of only one or a few genes are evaluated.

In a preferred embodiment, screens are designed to first find candidate agents that can bind to colorectal cancer proteins, and then these agents may be used in assays that evaluate the ability of the candidate agent to modulate colorectal cancer activity. Thus, as will be appreciated by those in the art, there are a number of different assays which may be run; binding assays and activity assays.

In a preferred embodiment, binding assays are done. In general, purified or isolated gene product is used; that is, the gene products of one or more colorectal cancer nucleic acids are made. In general, this is done as is known in the art. For example, antibodies are generated to the protein gene products, and standard immunoassays are run to determine the amount of protein present. Alternatively, cells comprising the colorectal cancer proteins can be used in the assays.

Thus, in a preferred embodiment, the methods comprise combining a colorectal cancer protein and a candidate bioactive agent, and determining the binding of the candidate agent to the colorectal cancer protein. Preferred embodiments utilize the human colorectal cancer protein, although other mammalian proteins may also be used, for example for the development of animal models of human disease. In some embodiments, as outlined herein, variant or derivative colorectal cancer proteins may be used.

Generally, in a preferred embodiment of the methods herein, the colorectal cancer protein or the candidate agent is non-diffusably bound to an insoluble support having isolated sample receiving areas (e.g. a microtiter plate, an array, etc.). It is understood that alternatively, soluble assays known in the art may be performed. The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

In a preferred embodiment, the colorectal cancer protein is bound to the support, and a candidate bioactive agent is added to the assay. Alternatively, the candidate agent is bound to the support and the colorectal cancer protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the colorectal cancer protein may be done in a number of ways. In a preferred embodiment, the candidate bioactive agent is labelled, and binding determined directly. For example, this may be done by attaching all or a portion of the colorectal cancer protein to a solid support, adding a labelled candidate agent (for example a fluorescent label), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}I$, or with fluorophores. Alternatively, more than one component may be labeled with different labels; using $^{125}I$ for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. colorectal cancer), such as an antibody, peptide, binding partner, ligand, etc. Under certain circumstances, there may be competitive binding as between the bioactive agent and the binding moiety, with the binding moiety displacing the bioactive agent.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the colorectal cancer protein and thus is capable of binding to, and potentially modulating, the activity of the colorectal cancer protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the colorectal cancer protein with a higher affinity. Thus, if the candidate bioactive agent is labeled, the presence of the label on the support, coupled with a lack of competitor binding, may indicate that the candidate agent is capable of binding to the colorectal cancer protein.

In a preferred embodiment, the methods comprise differential screening to identity bioactive agents that are capable of modulating the activity of the colorectal cancer proteins. In this embodiment, the methods comprise combining a colorectal cancer protein and a competitor in a first sample. A second sample comprises a candidate bioactive agent, a colorectal cancer protein and a competitor. The binding of the competitor is determined for both samples, and a change, or difference in binding between the two samples indicates the presence of an agent capable of binding to the colorectal cancer protein and potentially modulating its activity. That is, if the binding of the competitor is different in the second sample relative to the first sample, the agent is capable of binding to the colorectal cancer protein.

Alternatively, a preferred embodiment utilizes differential screening to identify drug candidates that bind to the native colorectal cancer protein, but cannot bind to modified colorectal cancer proteins. The structure of the colorectal cancer protein may be modeled, and used in rational drug design to synthesize agents that interact with that site. Drug candidates that affect colorectal cancer bioactivity are also identified by screening drugs for the ability to either enhance or reduce the activity of the protein.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of colorectal cancer proteins may also be done. In a preferred embodiment, methods for screening for a bioactive agent capable of modulating the activity of colorectal cancer proteins comprise the steps of adding a candidate bioactive agent to a sample of colorectal cancer proteins, as above, and determining an alteration in the biological activity of colorectal cancer proteins. "Modulating the activity" of colorectal cancer includes an increase in activity, a decrease in activity, or a change in the type or kind of activity present. Thus, in this embodiment, the candidate agent should both bind to colorectal cancer proteins (although this may not be necessary), and alter its biological or biochemical activity as defined herein. The methods include both in vitro screening methods, as are generally outlined above, and in vivo screening of cells for alterations in the presence, distribution, activity or amount of colorectal cancer proteins.

Thus, in this embodiment, the methods comprise combining a colorectal cancer sample and a candidate bioactive agent, and evaluating the effect on colorectal cancer activity. By "colorectal cancer activity" or grammatical equivalents herein is meant at least one of colorectal cancer's biological activities, including, but not limited to, cell division, preferably in colon tissue, cell proliferation, tumor growth, transformation of cells and serine protease activity. In one embodiment, colorectal cancer activity includes activation of CJA8 or a substrate thereof by CJA8. An inhibitor of colorectal cancer activity is an agent which inhibits any one or more colorectal cancer activities.

In a preferred embodiment, the activity of the colorectal cancer protein is increased; in another preferred embodiment, the activity of the colorectal cancer protein is decreased. Thus, bioactive agents that are antagonists are preferred in some embodiments, and bioactive agents that are agonists may be preferred in other embodiments.

In a preferred embodiment, the invention provides methods for screening for bioactive agents capable of modulating the activity of a colorectal cancer protein. The methods comprise adding a candidate bioactive agent, as defined above, to a cell comprising colorectal cancer proteins. Preferred cell types include almost any cell. The cells contain a recombinant nucleic acid that encodes a colorectal cancer protein. In a preferred embodiment, a library of candidate agents are tested on a plurality of cells.

In one aspect, the assays are evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In another example, the determinations are determined at different stages of the cell cycle process.

In this way, bioactive agents are identified. Compounds with pharmacological activity are able to enhance or interfere with the activity of the colorectal cancer protein. In one embodiment, "colorectal cancer protein activity" as used herein includes at least one of the following: colorectal cancer activity, binding to CJA8, activation of CJA8 or activation of substrates of CJA8 by CJA8. An inhibitor of CJA8 inhibits at least one of CJA8's bioactivities.

In one embodiment, a method of inhibiting colorectal cancer cell division is provided. The method comprises administration of a colorectal cancer inhibitor.

In another embodiment, a method of inhibiting colorectal tumor growth is provided. The method comprises administration of a colorectal cancer inhibitor. In a preferred embodiment, the inhibitor is an inhibitor of CJA8.

In a further embodiment, methods of treating cells or individuals with colorectal cancer are provided. The method comprises administration of a colorectal cancer inhibitor. In a preferred embodiment, the inhibitor is an inhibitor of CJA8.

In one embodiment, a colorectal cancer inhibitor is an antibody as discussed above. In another embodiment, the colorectal cancer inhibitor is an antisense molecule. Antisense molecules as used herein include antisense or sense oligonucleotides comprising a singe-stranded nucleic acid sequence (either RNA or DNA) capable of binding to target mRNA (sense) or DNA (antisense) sequences for colorectal cancer molecules. A preferred antisense molecule is for CJA8 or for a ligand or activator thereof. Antisense or sense oligonucleotides, according to the present invention, comprise a fragment generally at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Antisense molecules may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell. Alternatively, a sense or an antisense oligonucleotide may be introduced into a cell containing the target nucleic acid sequence by formation of an oligonucleotide-lipid complex, as described in WO 90/10448. It is understood that the use of antisense molecules or knock out and knock in models may also be used in screening assays as discussed above, in addition to methods of treatment.

The compounds having the desired pharmacological activity may be administered in a physiologically acceptable carrier to a host, as previously described. The agents may be administered in a variety of ways, orally, parenterally e.g., subcutaneously, intraperitoneally, intravascularly, etc. Depending upon the manner of introduction, the compounds may be formulated in a variety of ways. The concentration of therapeutically active compound in the formulation may vary from about 0.1–100 wt. %. The agents may be administered alone or in combination with other treatments, i.e., radiation.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Without being bound by theory, it appears that the various colorectal cancer sequences are important in colorectal cancer. Accordingly, disorders based on mutant or variant colorectal cancer genes may be determined. In one embodiment, the invention provides methods for identifying cells containing variant colorectal cancer genes comprising determining all or part of the sequence of at least one endogeneous colorectal cancer gene in a cell. As will be appreciated by those in the art, this may be done using any number of sequencing techniques. In a preferred embodiment, the invention provides methods of identifying the colorectal cancer genotype of an individual comprising determining all or part of the sequence of at least one colorectal cancer gene of the individual. This is generally done in at least one tissue of the individual, and may include the evaluation of a number of tissues or different samples of the same tissue. The method may include comparing the sequence of the sequenced gene to a known gene, i.e. a wild-type gene.

The sequence of all or part of the colorectal cancer gene can then be compared to the sequence of a known colorectal cancer gene to determine if any differences exist. This can be done using any number of known homology programs, such as Bestfit, etc. In a preferred embodiment, the presence of a difference in the sequence between the colorectal cancer gene of the patient and the known colorectal cancer gene is indicative of a disease state or a propensity for a disease state, as outlined herein.

In a preferred embodiment, the colorectal cancer genes are used as probes to determine the number of copies of the colorectal cancer gene in the genome.

In another preferred embodiment colorectal cancer genes are used as probed to determine the chromosomal localization of the colorectal cancer genes. Information such as chromosomal localization finds use in providing a diagnosis or prognosis in particular when chromosomal abnormalities such as translocations, and the like are identified in colorectal cancer gene loci.

Thus, in one embodiment, methods of modulating colorectal cancer in cells or organisms are provided. In one embodiment, the methods comprise administering to a cell an antibody that reduces or eliminates the biological activity of an endogenous colorectal cancer protein. Alternatively, the methods comprise administering to a cell or organism a recombinant nucleic acid encoding a colorectal cancer protein. As will be appreciated by those in the art, this may be accomplished in any number of ways. In a preferred embodiment, for example when the colorectal cancer sequence is down-regulated in colorectal cancer, the activity of the colorectal cancer gene is in creased by increasing the amount in the cell, for example by overexpressing the endogenous protein or by administering a gene encoding the sequence, using known gene-therapy techniques, for example. In a preferred embodiment, the gene therapy techniques include the incorporation of the exogenous gene using enhanced homologous recombination (EHR), for example as described in PCT/US93/03868, hereby incorporated by reference in its entirety. Alternatively, for example when the colorectal cancer sequence is up-regulated in colorectal cancer, the activity of the endogeneous gene is decreased, for example by the administration of an inhibitor of colorectal cancer, such as an antisense nucleic acid.

In one embodiment, the colorectal cancer proteins of the present invention may be used to generate polyclonal and monoclonal antibodies to colorectal cancer proteins, which are useful as described herein. Similarly, the colorectal cancer proteins can be coupled, using standard technology, to affinity chromatography columns. These columns may then be used to purify colorectal cancer antibodies. In a preferred embodiment, the antibodies are generated to epitopes unique to a colorectal cancer protein; that is, the antibodies show little or no cross-reactivity to other proteins. These antibodies find use in a number of applications. For example, the colorectal cancer antibodies may be coupled to standard affinity chromatography columns and used to purify colorectal cancer proteins. The antibodies may also be used as blocking polypeptides, as outlined above, since they will specifically bind to the colorectal cancer protein.

In one embodiment, a therapeutically effective dose of a colorectal cancer or modulator thereof is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The administration of the colorectal cancer proteins and modulators of the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the colorectal cancer proteins and modulators may be directly applied as a solution or spray.

The pharmaceutical compositions of the present invention comprise a colorectal cancer protein in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

In a preferred embodiment, colorectal cancer proteins and modulators are administered as therapeutic agents, and can be formulated as outlined above. Similarly, colorectal cancer genes (including both the full-length sequence, partial sequences, or regulatory sequences of the colorectal cancer coding regions) can be administered in gene therapy applications, as is known in the art. These colorectal cancer genes can include antisense applications, either as gene therapy (i.e. for incorporation into the genome) or as antisense compositions, as will be appreciated by those in the art.

In a preferred embodiment, colorectal cancer genes are administered as DNA vaccines, either single genes or combinations of colorectal cancer genes. Naked DNA vaccines are generally known in the art. Brower, Nature Biotechnology, 16:1304–1305 (1998).

In one embodiment, colorectal cancer genes of the present invention are used as DNA vaccines. Methods for the use of genes as DNA vaccines are well known to one of ordinary skill in the art, and include placing a colorectal cancer gene or portion of a colorectal cancer gene under the control of a promoter for expression in a patient with colorectal cancer. The colorectal cancer gene used for DNA vaccines can encode full-length colorectal cancer proteins, but more preferably encodes portions of the colorectal cancer proteins including peptides derived from the colorectal cancer protein. In a preferred embodiment a patient is immunized with a DNA vaccine comprising a plurality of nucleotide sequences derived from a colorectal cancer gene. Similarly, it is possible to immunize a patient with a plurality of colorectal cancer genes or portions thereof as defined herein. Without being bound by theory, expression of the polypeptide encoded by the DNA vaccine, cytotoxic T-cells, helper T-cells and antibodies are induced which recognize and destroy or eliminate cells expressing colorectal cancer proteins.

In a preferred embodiment, the DNA vaccines include a gene encoding an adjuvant molecule with the DNA vaccine. Such adjuvant molecules include cytokines that increase the immunogenic response to the colorectal cancer polypeptide encoded by the DNA vaccine. Additional or alternative adjuvants are known to those of ordinary skill in the art and find use in the invention.

In another preferred embodiment colorectal cancer genes find use in generating animal models of colorectal cancer. For example, as is appreciated by one of ordinary skill in the art, when the colorectal cancer gene identified is repressed or diminished in colorectal cancer tissue, gene therapy technology wherein antisense RNA directed to the colorectal cancer gene will also diminish or repress expression of the gene. An animal generated as such serves as an animal model of colorectal cancer that finds use in screening bioactive drug candidates. Similarly, gene knockout technology, for example as a result of homologous recombination with an appropriate gene targeting vector, will result in the absence of the colorectal cancer protein. When desired, tissue-specific expression or knockout of the colorectal cancer protein may be necessary.

It is also possible that the colorectal cancer protein is overexpressed in colorectal cancer. As such, transgenic animals can be generated that overexpress the colorectal cancer protein. Depending on the desired expression level, promoters of various strengths can be employed to express the transgene. Also, the number of copies of the integrated transgene can be determined and compared for a determination of the expression level of the transgene. Animals generated by such methods find use as animal models of colorectal cancer and are additionally useful in screening for bioactive molecules to treat disorders related to the colorectal cancer protein.

It is understood that the examples described herein in no way serve to limit the true scope of this invention, but rather are presented for illustrative purposes. All references and sequences of accession numbers cited herein are incorporated by reference in their entirety.

EXAMPLES

Example 1

Tissue Preparation, Labeling Chips, and Fingerprints

Purify Total RNA from Tissue Using TRIzol Reagent

Estimate tissue weight. Homogenize tissue samples in 1 ml of TRIzol per 50 mg of tissue using a Polytron 3100 homogenizer. The generator/probe used depends upon the tissue size. A generator that is too large for the amount of tissue to be homogenized will cause a loss of sample and lower RNA yield. Use the 20 mm generator for tissue weighing more than 0.6 g. If the working volume is greater than 2 ml, then homogenize tissue in a 15 ml polypropylene tube (Falcon 2059). Fill tube no greater than 10 ml.

Homogenization

Before using generator, it should have been cleaned after last usage by running it through soapy $H_2O$ and rinsing thoroughly. Run through with EtOH to sterilize. Keep tissue frozen until ready. Add TRIzol directly to frozen tissue then homogenize.

Following homogenization, remove insoluble material from the homogenate by centrifugation at 7500×g for 15 min. in a Sorvall superspeed or 12,000×g for 10 min. in an Eppendorf centrifuge at 4° C. Transfer the cleared homogenate to a new tube(s). The samples may be frozen now at −60 to −70° C. (and kept for at least one month) or you may continue with the purification.

Phase Separation

Incubate the homogenized samples for 5 minutes at room temperature. Add 0.2 ml of chloroform per 1 ml of TRIzol reagent used in the original homogenization. Cap tubes securely and shake tubes vigorously by hand (do not vortex) for 15 seconds. Incubate samples at room temp. for 2–3 minutes. Centrifuge samples at 6500 rpm in a Sorvall superspeed for 30 min. at 4° C. (You may spin at up to 12,000×g for 10 min. but you risk breaking your tubes in the centrifuge.)

RNA Precipitation

Transfer the aqueous phase to a fresh tube. Save the organic phase if isolation of DNA or protein is desired. Add 0.5 ml of isopropyl alcohol per 1 ml of TRizol reagent used in the original homogenization. Cap tubes securely and invert to mix. Incubate samples at room temp. for 10 minutes. Centrifuge samples at 6500 rpm in Sorvall for 20 min. at 4° C.

RNA Wash

Pour off the supernate. Wash pellet with cold 75% ethanol. Use 1 ml of 75% ethanol per 1 ml of TRIzol reagent used in the initial homogenization. Cap tubes securely and invert several times to loosen pellet. (Do not vortex). Centrifuge at <800 rpm (<7500×g) for 5 minutes at 4° C. Pour off the wash. Carefully transfer pellet to an eppendorf tube (let it slide down the tube into the new tube and use a pipet tip to help guide it in if necessary). Depending on the volumes you are working with, you can decide what size tube(s) you want to precipitate the RNA in. When I tried leaving the RNA in the large 15 ml tube, it took so long to dry (i.e. it did not dry) that I eventually had to transfer it to a smaller tube. Let pellet dry in hood. Resuspend RNA in an appropriate volume of DEPC $H_2O$. Try for 2–5 ug/ul. Take absorbance readings.

Purify Poly A+ mRNA from Total RNA or Clean Up Total RNA with Qiagen's RNeasy Kit Purification of poly $A^+$ mRNA from total RNA. Heat oligotex suspension to 37° C. and mix immediately before adding to RNA. Incubate Elution Buffer at 70° C. Warm up 2×Binding Buffer at 65° C. if there is precipitate in the buffer. Mix total RNA with DEPC-treated water, 2×Binding Buffer, and Oligotex according to Table 2 on page 16 of the Oligotex Handbook. Incubate for 3 minutes at 65° C. Incubate for 10 minutes at room temperature. Centrifuge for 2 minutes at 14,000 to 18,000 g. If centrifuge has a "soft setting," then use it. Remove supernatant without disturbing Oligotex pellet. A little bit of solution can be left behind to reduce the loss of Oligotex. Save sup until certain that satisfactory binding and elution of poly A mRNA has occurred.

Gently resuspend in Wash Buffer OW2 and pipet onto spin column. Centrifuge the spin column at full speed (soft setting if possible) for 1 minute.

Transfer spin column to a new collection tube and gently resuspend in Wash Buffer OW2 and centrifuge as describe herein.

Transfer spin column to a new tube and elute with 20 to 100 ul of preheated (70° C.) Elution Buffer. Gently resuspend Oligotex resin by pipetting up and down. Centrifuge as above. Repeat elution with fresh elution buffer or use first eluate to keep the elution volume low.

Read absorbance, using diluted Elution Buffer as the blank.

Before proceeding with cDNA synthesis, the mRNA must be precipitated. Some component leftover or in the Elution Buffer from the Oligotex purification procedure will inhibit downstream enzymatic reactions of the mRNA.

Ethanol Precipitation

Add 0.4 vol. of 7.5 M $NH_4OAc$+2.5 vol. of cold 100% ethanol. Precipitate at −20° C. 1 hour to overnight (or 20–30 min. at −70° C.). Centrifuge at 14,000–16,000×g for 30 minutes at 4 pellet with 0.5 ml of 80%ethanol (−20° C.) then centrifuge at 14,000–16,000×g for 5 minutes at room temperature. Repeat 80% ethanol wash. Dry the last bit of ethanol from the pellet in the hood. (Do not speed vacuum). Suspend pellet in DEPC $H_2O$ at 1 µg/ul concentration.

Clean Up Total RNA Using Qiagen's RNeasy Kit

Add no more than 10 ug to an RNeasy column. Adjust sample to a volume of 100 ul with RNase-free water. Add 350 ul Buffer RLT then 250 ul ethanol (100%) to the sample. Mix by pipetting (do not centrifuge) then apply sample to an RNeasy mini spin column. Centrifuge for 15 sec at >10,000 rpm. If concerned about yield, re-apply flowthrough to column and centrifuge again.

Transfer column to a new 2-ml collection tube. Add 500 ul Buffer RPE and centrifuge for 15 sec at >10,000 rpm. Discard flowthrough. Add 500 ul Buffer RPE and centrifuge for 15 sec at >10,000 rpm. Discard flowthrough then centrifuge for 2 min at maximum speed to dry column membrane. Transfer column to a new 1.5-ml collection tube and apply 30–50 ul of RNase-free water directly onto column membrane. Centrifuge 1 min at >10,000 rpm. Repeat elution. Take absorbance reading. If necessary, ethanol precipitate with ammonium acetate and 2.5×volume 100% ethanol.

Make cDNA Using Gibco's "SuperScript Choice System for cDNA Synthesis" Kit First Strand cDNA Synthesis Use 5 ug of total RNA or 1 ug of polyA+ mRNA as starting material. For total RNA, use 2 ul of SuperScript RT. For polyA+ mRNA, use 1 ul of SuperScript RT. Final volume of first strand synthesis mix is 20 ul. RNA must be in a volume no greater than 10 ul. Incubate RNA with 1 ul of 100 pmol T7–T24 oligo for 10 min at 70 C. On ice, add 7 ul of: 4 ul 5×$1^{st}$ Strand Buffer, 2 ul of 0.1M DTT, and 1 ul of 10 mM dNTP mix. Incubate at 37 C. for2 min then add SuperScript RT Incubate at 37 C. for 1 hour.

Second Strand Synthesis

Place $1^{st}$ strand reactions on ice.

Add:

91 ul DEPC H20

30 ul 5×$2^{nd}$ Strand Buffer 3 ul 10 mM dNTP mix 1 ul 10 U/ul *E.coli* DNA Ligase 4 ul 10 U/ul *E.coli* DNA Polymerase 1 ul 2 U/ul RNase H Make the above into a mix if there are more than 2 samples. Mix and incubate 2 hours at 16 C. Add 2 ul T4 DNA Polymerase. Incubate 5 min at 16 C. Add 10 ul of 0.5M EDTA Clean Up cDNA Phenol:Chloroform:Isoamyl Alcohol (25:24:1) purification using Phase-Lock gel tubes: Centrifuge PLG tubes for 30 sec at maximum speed. Transfer cDNA mix to PLG tube. Add equal volume of phenol:chloroform:isamyl alcohol and shake vigorously (do not vortex). Centrifuge 5 minutes at maximum speed. Transfer top aqueous solution to a new tube. Ethanol precipitate: add 7.5×5M NH4Oac and 2.5× volume of 100% ethanol. Centrifuge immediately at room temp. for 20 min, maximum speed. Remove sup then wash pellet 2× with cold 80% ethanol. Remove as much ethanol wash as possible then let pellet air dry. Resuspend pellet in 3 ul RNase-free water.

In vitro Transcription (IVT) and Labeling with Biotin

Pipet 1.5 ul of cDNA into a thin-wall PCR tube.

Make NTP Labeling Mix

| Combine at room temperature: | 2 ul | T7 10xATP (75 mM) (Ambion) |
|---|---|---|
| | 2 ul | T7 10xGTP (75 mM) (Ambion) |
| | 1.5 ul | T7 10xCTP (75 mM) (Ambion) |
| | 1.5 ul | T7 10xUTP (75 mM) (Ambion) |
| | 3.75 ul | 10 mM Bio-11-UTP (Boehringer-Mannheim/Roche or Enzo) |
| | 3.75 ul | 10 mM Bio-16-CTP (Enzo) |
| | 2 ul | 10x T7 transcription buffer (Ambion) |
| | 2 ul | 10x T7 enzyme mix (Ambion) |

Final volume of total reaction is 20 ul. Incubate 6 hours at 37° C. in a PCR machine.

RNeasy Clean-up of IVT Product

Follow previous instructions for RNeasy columns or refer to Qiagen's RNeasy protocol handbook.

cRNA will most likely need to be ethanol precipitated. Resuspend in a volume compatible with the fragmentation step.

Fragmentation 15 ug of labeled RNA is usually fragmented. Try to minimize the fragmentation reaction volume; a 10 ul volume is recommended but 20 ul is all right. Do not go higher than 20 ul because the magnesium in the fragmentation buffer contributes to precipitation in the hybridization buffer. Fragment RNA by incubation at 94 C for 35 minutes in 1×Fragmentation buffer.

5×Fragmentation Buffer 200 mM Tris-acetate, pH 8.1

500 mM KOAc 150 mM MgOAc

The labeled RNA transcript can be analyzed before and after fragmentation. Samples can be heated to 65 C. for 15 minutes and electrophoresed on 1% agarose/TBE gels to get an approximate idea of the transcript size range.

Hybridization 200 ul (10 ug cRNA) of a hybridization mix is put on the chip. If multiple hybridizations are to be done (such as cycling through a 5 chip set), then it is recommended that an initial hybridization mix of 300 ul or more be made.

Hybrization Mix: Fragment Labeled RNA (50 ng/ul Final Conc.)

50 pM 948-b control oligo 1.5 pM BioB 5 pM BioC 25 pM BioD 100 pM CRE 0.1 mg/ml herring sperm DNA 0.5 mg/ml acetylated BSA to 300 ul with 1×MES hyb. buffer The instruction manuals for the products used herein are incorporated herein in their entirety.

| Labeling Protocol Provided Herein | |
|---|---|
| Hybridization reaction: | |
| Start with non-biotinylated IVT (purified by RNeasy columns) (see example 1 for steps from tissue to IVT) | |
| IVT antisense RNA; 4 µg: | µl |
| Random Hexamers (1 µg/µl): | 4 µl |

| -continued | |
|---|---|
| Labeling Protocol Provided Herein | |
| H$_2$O: | µl |
| | 14 µl |

Incubate 70° C., 10 min. Put on ice.

Reverse Transcription

| 5X First Strand (BRL) buffer: | 6 µl |
|---|---|
| 0.1 M DTT: | 3 µl |
| 50X dNTP mix: | 0.6 µl |
| H$_2$O: | 2.4 µl |
| Cy3 or Cy5 dUTP (1 mM): | 3 µl |
| SS RT II (BRL): | 1 µl |
| | 16 µl |

Add to hybridization reaction.

Incubate 30 min., 42° C.

Add 1 µl SSII and let go for another hour.

Put on ice.

50×dNTP mix (25 mM of cold dATP, dCTP, and dGTP, 10 mM of dTTP: 25 µi each of 100 mM dATP, dCTP, and dGTP; 10 µl of 100 mM dTTP to 15 µl H2O. dNTPs from Pharmacia)

RNA Degradation

| - Add 1.5 µl 1M NaOH/2 mM EDTA, incubate at 65° C., 10 min. | 86 µl H$_2$O |
|---|---|
| | 10 µl 10N NaOH |
| | 4 µl 50 mM EDTA |

U-Con 30

500 µl TE/sample spin at 7000 g for 10 min, save flow through for purification

Qiagen Purification suspend u-con recovered material in 500 µl buffer PB proceed w/ normal Qiagen protocol DNAse Digest Add 1 µl of 1/100 dil of DNAse/30 µl Rx and incubate at 37° C. for 15 min.

5 min 95° C. to denature enzyme

Sample Preparation

| -Add: | |
|---|---|
| Cot-1 DNA: | 10 µl |
| 50X dNTPs: | 1 µl |
| 20X SSC: | 2.3 µl |
| Na pyro phosphate: | 7.5 µl |
| 10 mg/ml Herring sperm DNA | 1 µl of 1/10 dilution |
| | 21.8 final vol. |

Dry down in speed vac.

Resuspend in 15 µl H$_2$O.

Add 0.38 μl 10% SDS.
Heat 95° C., 2 min.
Slow cool at room temp. for 20 min.
Put on slide and hybridize overnight at 64° C.
Washing After the Hybridization

| 3X SSC/0.03% SDS: | 2 min. 37.5 mls 20X SSC + 0.75 mls 10% SDS in 250 mls H$_2$O |
|---|---|
| 1X SSC: 5 min. | 12.5 mls 20X SSC in 250 mls H$_2$O |
| 0.2X SSC: 5 min. | 2.5 mls 20X SSC in 250 mls H$_2$O |

Dry slides in centrifuge, 1000 RPM, 1 min.

Scan at appropriate PMT's and channels.

Example 2

Expression studies were performed herein. As indicated in FIG. 3, CJA8 is upregulated in colorectal cancer tissue. CJA8 is located on chromosome 11.

We claim:

1. A method of diagnosing colorectal cancer comprising:
   a) determining the expression of a gene encoding CJA8 or a fragment thereof in a first colon tissue of a first individual; and
   b) comparing said expression of said gene(s) to the expression of a gene encoding CJA8 or a fragment thereof in a second normal tissue from said first individual or in a tissue from a second unaffected individual;
   wherein a difference in said expression indicates that the first individual has colorectal cancer.

2. The method of claim 1, wherein said second normal tissue of said first individual is colorectal tissue.

3. The method of claim 2, wherein a difference between expression in said first colon tissue and said second normal tissue indicates that the first individual has colorectal cancer.

4. The method of claim 1, wherein said second normal tissue of said first individual is not colorectal tissue.

5. The method of claim 4, wherein a difference between expression in said first colon tissue and said second normal tissue indicates that the first individual has colorectal cancer.

6. The method of claim 1, wherein said tissue of said second unaffected individual is normal colorectal tissue.

7. The method of claim 6, wherein a difference between expression in said first colon tissue and said tissue of said second unaffected individual indicates that the first individual has colorectal cancer.

8. The method of claim 1, wherein said tissue of said second unaffected individual is colorectal cancer tissue.

9. The method of claim 8, wherein a similarity between expression in said first colon tissue and said tissue of said second unaffected individual indicates that the first individual has colorectal cancer.

10. The method of claim 1, wherein said determining is by measuring RNA encoding CJA8.

11. The method of claim 10, wherein said measuring utilizes a biochip comprising a nucleic acid comprising the sequence of FIG. 1 (SEQ ID NO:1) or a fragment thereof.

12. The method of claim 10, wherein said RNA encoding CJA8 comprises the RNA equivalent of the sequence as disclosed in FIG. 1 (SEQ ID NO:1) or a fragment thereof.

13. The method of claim 1, wherein said determining is by measuring CJA8 protein.

14. The method of claim 13, wherein said measuring CJA8 protein comprises binding of CJA8 with an antibody.

15. The method of claim 14, wherein said antibody specifically binds a polypeptide comprising the sequence as disclosed in FIG. 2 (SEQ ID NO:2) or a fragment thereof.

16. A method of diagnosing colorectal cancer comprising:
a) determining the expression of a gene encoding CJA8 in a first colon tissue of a first individual; and
b) comparing said expression of said gene(s) to the expression of a gene encoding CJA8 in a second normal tissue from said first individual or in a tissue from a second unaffected individual;

wherein a difference in said expression indicates that the first individual has colorectal cancer.

* * * * *